United States Patent
Lee et al.

(10) Patent No.: US 8,992,534 B2
(45) Date of Patent: Mar. 31, 2015

(54) METHOD AND SYSTEM FOR CUTTING KNEE JOINT USING ROBOT

(75) Inventors: Chun Tek Lee, Suwon-si (KR); Sung Hwan Yoon, Seoul (KR); Oh Myoung Kwon, Hwaseong-si (KR); Joon Sik Park, Seoul (KR); Hang Jae Lee, Ansan-si (KR); Mi Ro Kang, Seoul (KR); Masei Marty Trabish, Yongin-si (KR); Jai Karan, Fremont, CA (US)

(73) Assignees: Chun Tek Lee, Gyeonggi-Do (KR); Masei Marty Trabish, Gyeonggi-Do (KR)

( * ) Notice: Subject to any disclaimer, the term of this patent is extended or adjusted under 35 U.S.C. 154(b) by 0 days.

(21) Appl. No.: 13/368,889

(22) Filed: Feb. 8, 2012

(65) Prior Publication Data

US 2012/0165830 A1    Jun. 28, 2012

Related U.S. Application Data

(63) Continuation of application No. 12/218,679, filed on Jul. 17, 2008, now abandoned.

(30) Foreign Application Priority Data

May 16, 2008 (KR) .................. 10-2008-0045684

(51) Int. Cl.
- *A61B 17/32* (2006.01)
- *A61B 17/16* (2006.01)
- *A61B 19/00* (2006.01)
- *A61B 17/56* (2006.01)

(52) U.S. Cl.
CPC ......... *A61B 17/1633* (2013.01); *A61B 17/1615* (2013.01); *A61B 17/1675* (2013.01); *A61B 19/2203* (2013.01); *A61B 2017/564* (2013.01)
USPC ........................................ 606/80

(58) Field of Classification Search
USPC ..................................... 606/79–85
See application file for complete search history.

(56) References Cited

U.S. PATENT DOCUMENTS

| | | | |
|---|---|---|---|
| 3,565,192 A * | 2/1971 | McLarty | 175/246 |
| 4,612,922 A | 9/1986 | Barber | |
| 5,505,737 A * | 4/1996 | Gosselin et al. | 606/79 |
| 5,806,518 A | 9/1998 | Mittelstadt | |
| 5,921,728 A | 7/1999 | Kammeraad et al. | |
| 6,237,070 B1 | 5/2001 | Ng | |
| 6,258,093 B1 | 7/2001 | Edwards et al. | |
| 2002/0029045 A1* | 3/2002 | Bonutti | 606/86 |
| 2004/0199167 A1 | 10/2004 | Fletcher et al. | |
| 2005/0075639 A1 | 4/2005 | Lechot | |
| 2006/0030853 A1* | 2/2006 | Haines | 606/79 |

* cited by examiner

*Primary Examiner* — Matthew Lawson
*Assistant Examiner* — Zade Coley
(74) *Attorney, Agent, or Firm* — Patrick J. S. Inouye; Krista A. Wittman

(57) ABSTRACT

A method and a system for cutting the knee joint using a robot. A cantilevered cutter is introduced into the knee joint from inside and outside of upper and lower bones of the knee joint to realize a tunnel cutting technique in which cutting is conducted such that tunnels are defined in bone and remnant bone is cleared. The cutter includes a shaft in which a substantial axial portion is fitted into a sleeve and a remaining axial portion serves as a cantilever extending out of the sleeve, and a head which is formed at a distal end of the shaft. A length of the cantilever and a diameter of the head are determined to have minimum sizes as long as the head can be introduced into bone in such a way as to define a tunnel and can be moved in the bone while cutting the bone.

12 Claims, 37 Drawing Sheets

METHOD AND SYSTEM FOR CUTTING KNEE JOINT USING ROBOT

CROSS REFERENCE TO PRIOR APPLICATIONS

The present application claims under 35 U.S.C. §120 the benefits of a prior filed nonprovisional patent application Ser. No. 12/218,679 (filed on Jul. 17, 2008) which claims priority to Korean Patent Application No. 10-2008-0045684 (filed on May 16, 2008), which are all hereby incorporated by reference in their entirety.

BACKGROUND OF THE INVENTION

1. Field of the Invention

The present invention relates to surgery using a robot, and more particularly, to a method and a system for cutting the knee joint using a robot, wherein a surface, on which an artificial joint is to be coupled to the knee joint, can be formed with maximum safety and high precision in implementing total knee replacement arthroplasty while minimizing the incision, of the skin by the robot without causing damage to the tissue around the patella.

2. Description of the Related Art

These days, as old age population increases, arthritis and osteoporotic hip fracture tend to increase.

In this regard, by directly implementing knee replacement arthroplasty rather than using an indirect therapy such as parmacotherapy, physical therapy and intra-articular injection therapy, which is mainly used in the past, early mobilization is enabled without pain. Also, with the development of joint mechanics, the lifetime of an artificial joint is increased over 20 years.

In spite of the nonoperative treatment as conservative treatment such as parmacotherapy, physical therapy and intra-articular injection therapy, when no symptom improvement is observed and the change of the joint continuously proceeds in such a way as to impede leading of everyday life, operative treatment is conducted.

By appropriately selecting operative treatment depending upon the age and the state of the joint, satisfactory results can be obtained.

The operative treatment includes arthroscopy, osteotomy, chondrocyte transplantation, and arthroplasty. A serious patient must receive arthroplasty.

The indication of arthroplasty for arthritis is when a patient's leg is curved and the effect of a medicine immediately disappears and the patient feels a pain even after taking the medicine.

In arthroplasty which is currently and directly conducted by a surgeon, since bone milling is not precise, it is difficult to precisely insert an artificial joint. Also, due to the imprecise insertion of the artificial joint, various complications may arise, and because the lifetime of the artificial joint is not so long, inconvenience is caused in that it is necessary to conduct surgery again some time in the future.

Recently, due to the development of a material and a surgery technique, the lifetime of the artificial joint has been increased over 20 years, and unicompartmental arthroplasty is also conducted such that the knee is incised by only about 6~7 cm and only a portion of the knee joint suffering from serious arthritis is replaced with an artificial joint.

The arthroplasty of the knee joint (which is the joint placed among the lower end of the femur, the upper end of the tibia, and the rear surface of the patella) is also called replacement arthroplasty, knee joint replacement or total knee replacement arthroplasty. The arthroplasty indicates the replacement of the original knee joint with an artificial joint made of faux metal, plastic or ceramic. Actually, the arthroplasty indicates the surgery of cutting the knee joint including the cartilage which covers the end of the bone, by about 8~9 mm and inserting the artificial joint therein.

The existing arthroplasty is conducted in a manner such that a master surgeon conducts surgery by milling out the bone directly using surgery instruments including a surgical drill, etc. This approach requires a substantial amount of incision of the skin and the flesh, and the precise milling of the stronger bone and the minimization of the damage to the bone are important in conducting the surgery. However, in the case that master surgeon directly conduct surgery, since it is difficult to handle precisely the surgery instruments and mill precisely the bone, an excessive amount of the bone is likely to be damaged during the milling of the bone or surrounding tissue is likely to be damaged.

In order to cope with these problems, there has been disclosed a method for milling the knee joint using a robot, that is, knee joint arthroplasty using a robot, in which the path of a rotary type cutter mounted to the distal end of a position-changeable arm of a robot is controlled in conformity with the information inputted to a computer so as to mill sequentially the bone of the knee joint so that planes, to which an artificial knee joint, i.e., an implant is to be coupled, are formed on the bone.

FIG. 39 illustrates a cutting system which is used in a conventional knee joint milling method using a robot.

Referring to FIG. 39, a rotary type cutter 100 mounted to the distal end of a position-changeable arm of a robot has a head 110 which is formed with cutting edges on the circumferential outer surfaces and the distal end surface thereof and has a diameter of 7.8 mm and a shaft 120 which extends from the head 110 and has the shape of a round bar and a diameter of 2.3 mm. The proximal end of the shaft 120 is connected to a motor M which is installed on the distal end of the position-changeable arm of the robot. The circumferential outer surface of the shaft 120 is rotatably supported in a sleeve 130 which is secured to the housing of the motor M so that quivering or bending does not occur while the shaft 120 rotates. The head 110 is positioned out of the sleeve 130 so that the bone can be milled through the rotation of the head 110.

As shown in FIG. 40, the conventional knee joint milling method using a robot adopts a top down milling scheme in that the cutter 100 approaches the knee joint from the anterior side of the knee joint and is moved repeatedly along the locus indicated by the arrows so that the bone can be gradually milled level by level by the head 110.

However, although the conventional method and the system contribute to some extent to the improvement in the precision of the surgery, they suffer from defects as described below.

That is to say, in the conventional method and system for cutting the knee joint using a robot, the entire shaft 120 of the cutter 100 for milling the bone is supported by the sleeve 130, the head 110 of the cutter 100 has a large size, and the head 110 approaches the knee joint from the anterior side of the knee joint and is rotated while drawing the large locus only in a lateral direction so that the bone can be milled by the head 110. Because of these facts, in order to avoid interference or impingement between the sleeve 130 and the head 110 and the skin tissue of the human body, a substantial amount of the skin and the flesh should be incised.

Also, due to the rotation of the head 110 having the large size, it is difficult to properly protect the important tissue such as the periosteum attached to the bone, and serious damage to the bone can be caused. Moreover, because a substantial amount of foreign substance such as bone particles are produced during milling, a surgery condition is deteriorated, and as the bone particles are introduced into the surrounding tissue, an inflammation may be caused after conducting the surgery, which can lead to a sequela of the surgery.

Further, since the conventional method and system adopt the top down milling scheme in which the bone is gradually milled out level by level, a lengthy period of milling time is required and a surgery time is extended as well. Due to this fact, the patient can feel severe pain even after the surgery, and the recovery of the patient can be retarded.

In addition, while the conventional level to level milling method has a characteristic in terms of precision, the patient and the master surgeon who has performed the surgery cannot be satisfied only with the precision. In order to provide enough satisfaction, the patient can walk within several hours without feeling pain after the surgery is completed and the patient comes out of the anesthetic.

Meanwhile, the conventional minimal invasive replacement surgery by the direct surgery of a surgeon confers advantages in that the skin is incised to a lesser degree so that the damage to the muscle and soft tissue can be minimized. Nevertheless, since the surgery is performed in a narrow space, the tissue is excessively retracted and therefore is likely to be damaged. Also, due to the incision of the skin to the lesser degree, the field of view becomes narrow, and it is difficult to insert precisely the implant.

SUMMARY OF THE INVENTION

Accordingly, the present invention has been made in an effort to solve the problems occurring in the related art, and an object of the present invention is to provide a method for cutting the knee joint using a robot wherein, in place of the conventional total knee replacement arthroplasty using a robot in which a cutter is moved only in the leftward and rightward directions from the anterior side of the knee joint when milling the bone using the robot, minimal invasive replacement surgery is combined with the total knee replacement arthroplasty using a robot to realize a surgical method based on a tunnel cutting technique in which a cutter is introduced not only from the anterior side of the knee joint but also outside or inside from the posterior center of the knee joint while defining an angle and cuts the bone, so that the minimal incision of the skin is required and the damage to the important tissue such as the skin, the flesh, the muscle and the bone, which is likely to be caused during the surgery, can be minimized and the surgery can be performed in a quick and efficient manner to obtain agreeable clinical results after the completion of the surgery and provide satisfaction to a patient, and a system for cutting the knee joint using a robot wherein, in order to realize the cutting method, the cutter is optimized to have a minimal diameter for permitting the cutting of bone tissue and a maximum length in consideration of the breakage, quivering, etc. of the cutter due to cutting resistance induced when cutting the bone.

In order to achieve the above object, according to one aspect of the present invention, there is provided a method for cutting the knee joint using a robot, wherein, when cutting the knee joint to implement total knee replacement arthroplasty, a cantilevered cutter having a small diameter is used and is introduced into the knee joint from inside and outside of upper and lower bones of the knee joint to realize a tunnel cutting technique in which cutting is conducted such that tunnels are defined in a bone and remnant bone is cleared, and wherein, when the upper bone of the knee joint is cut by moving the cutter toward the inside, the cutter is moved while being kept parallel to the Whiteside's line, and when the upper bone of the knee joint is cut by moving the cutter toward the outside, the cutter is moved while being slanted to a prescribed angle with respect to the Whiteside's line so as to avoid impingement between the cutter and surrounding tissue such as the patella and the ligament structure.

Here, preferably, while forming a tunnel by cutting the upper bone of the knee joint, the remnant bone serves as a natural safety shield which prevents the cutter from projecting out of the bone and damaging surrounding soft tissue.

Also, when cutting the lower bone of the knee joint, cutting is conducted through three cutting stages in which the cutter is inserted in different directions, for example, in a normal direction, a sideward direction and a diagonal direction, to form a single plane.

Preferably, when cutting the distal surface of the lower bone of the knee joint, the formation of the plane is effected by moving the cutter inward in a zigzag pattern, and in order to prevent surrounding soft tissue from being damaged, cutting is conducted such that a safety rim is left on the edge of the plane.

In order to achieve the above object, according to another aspect of the present invention, there is provided a system for cutting the knee joint using a robot, including a position-changeable arm, a motor provided to the distal end of the arm, a sleeve secured to the housing of the motor, and a cutter coupled to the shaft of the motor and rotatably supported in the sleeve, wherein the cutter includes a shaft which has the shape of a round bar and in which a substantial axial portion thereof is fitted into the sleeve to be rotated by the motor and a remaining axial portion thereof serves as a cantilever extending out of the sleeve, and a head which is formed at the distal end of the shaft extending out of the sleeve, and wherein the length of the cantilever of the shaft and the diameter of the head are determined to define a shape having minimum sizes as long as the head can be introduced into the bone in such a way as to define a tunnel and can be moved in the bone while cutting the bone, for example, a shape in which the diameter of the cantilever is 1.5~4.0 mm and the length thereof is 20~30 mm or a shape in which the diameter of the cantilever is 4.0~6.0 mm and the length thereof is 70~80 mm.

Here, it is preferred that the cutter have chatter blockers for preventing chattering during cutting and a prescribed helix angle to ensure easy discharge of chips and be made of a material having a hardness in the range of HRC80~120.

BRIEF DESCRIPTION OF THE DRAWINGS

The above objects, and other features and advantages of the present invention will become more apparent after a reading of the following detailed description taken in conjunction with the drawings, in which.

DETAILED DESCRIPTION OF PREFERRED EMBODIMENTS

Figure 1:
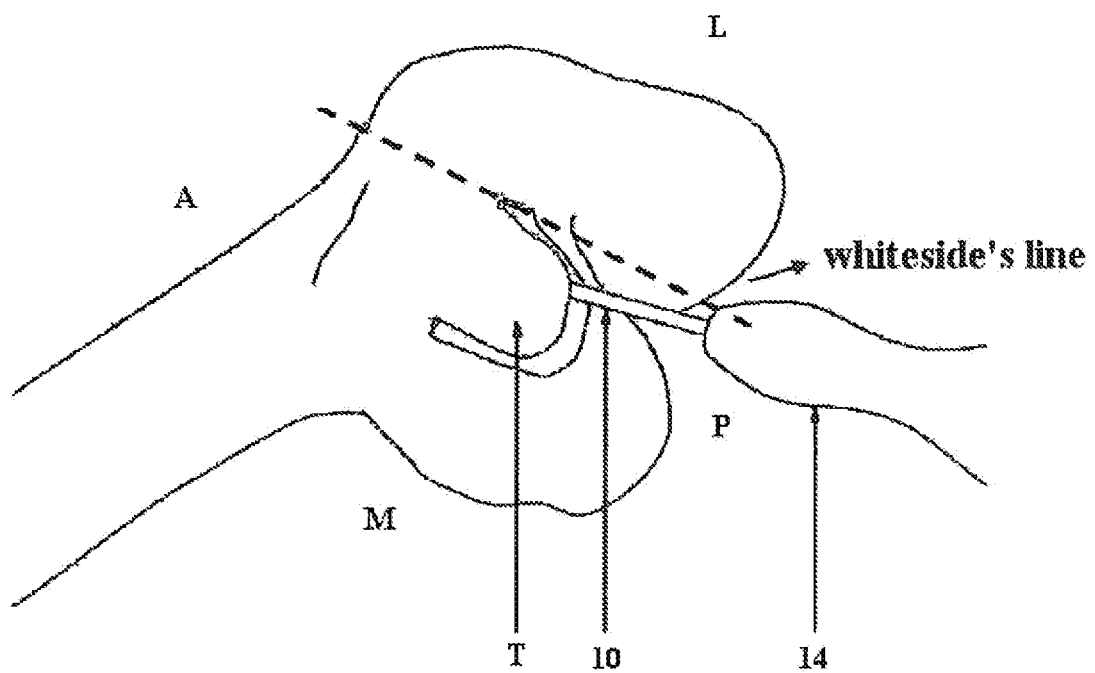
FIGS. 1 through 29 are schematic views illustrating the respective cutting steps of a method for cutting the knee joint using a robot in accordance with one embodiment of the present invention.

The present invention includes all devices for the positioning, the moving and the force feedback mechanisms of a cutting system mounted to the distal end of a robot to implement minimal/less invasive surgery. Also, the present invention includes the devices which are arranged on the distal end of the robot having multi-degree of freedom and perform a cutting operation, the devices involving a power generation device, a power transmission device, a sensor for monitoring cutting force applied to an end effecter, and cutters having various diameters necessary for cutting bone.

Also, the present invention includes a cutting system which involves a short cantilevered rotary cutter for minimal incision, and a tunnel type cutting method.

Moreover, the present invention includes chatter blockers (chatter prevention technology) which are formed on the distal end of the head of the cantilevered cutter, the retention of a helix angle of 10~20° on the circumferential outer surface of the cutter head for ensuring easy discharge of chips, the maintenance of the hardness of the material of the cutter in the range of HRC80~120 (HRC: hardness Rockwell), and a system design as to withstand chattering, quivering and vibration due to a density difference in bone (between cortical bone and cancellous bone).

The present invention includes all cutting paths and cutting operations along and by which the small cantilevered rotary cutter reaches the upper and lower bones of the knee joint when implementing the total knee joint replacement arthroplasty.

Thus, the present invention provides a system which can cut the bone through simple skin elevation instead of extensive skin retraction so that the damage to the skin tissue can be minimized and a surgical procedure can be completed in a hazard-free environment through the least possible incision size.

That is to say, the present invention includes the cutting method and the cutting system which can ensure safety through minimal incision.

To this end, in the cutter of a cutting system provided in accordance with one embodiment of the present invention, in order to minimize the size of a cut surface and cutting vibrations when cutting the bone, the cutter has a reduced diameter of 2.36 mm, and the head and the shaft of the cutter have the same diameter.

Also, the ideal length of the cantilever of the cutter for cutting the bone, that is, the length of the free end portion of the cutter shaft, which projects from a sleeve for holding the cutter, is set to an optimal length that can reach the extremities of prescribed bony surface cuts.

In other words, in the case of the cutter having the optimum diameter of 2.36 mm, it is most preferred that the length of the cantilever be set to 20~30 mm when measured from the distal end of the sleeve. Here, the cantilever of the cutter performs almost all of the cutting operation.

The reason why the ideal length of the cantilever is set to 20~30 mm in the present invention as described above resides in that, in consideration of the radius of the lower bone of the knee joint which corresponds to about 50 mm and the introduction angle of the cantilever attached to the arm of the robot depending upon a tunnel cutting style, in the present invention, all plane surfaces are not cut at once, and instead, partial cutting is conducted by dividing the cutting operation into five procedures so that the impingement between the cutter and surrounding tissue can be maximally avoided. Due to this partial cutting, as the size of a plane surface to be cut is decreased, the stress induced in the cutter can be reduced, and the vibrations transferred to the cutter can be minimized, as a result of which the diameter of the cutter can be minimized.

Because the partial cutting is conducted as described above, a miniature cutter can be fabricated and used. As a consequence, the cutter is prevented from being bent or quivering, a minimal cut surface can be provided through cutting, and the vibrations of the cutter can be significantly reduced so that the influence exerted to the surrounding tissue can be minimized.

Further, in the present invention, due to the tunnel cutting method, the thickness of a portion of the bone, which is removed through primary cutting by the cutter, is minimized, and the remnant bone can be left while having a substantial thickness. Hence, the cutter can be separated from the surrounding skin tissue by the thickness of the remnant bone, and the remnant bone can serve as a safety shield between the cutter and the surrounding soft tissue so that the transmission of the vibration of the cutter can be minimized and the stability of the surgery can be maximized.

In order to remove the bone in a more efficient manner through cutting, the chatter blockers are provided to the distal end of the cutter head. The chatter blockers perform the function of decreasing the quivering of the cutter when cutting the bone and increasing the cutting speed.

At this time, the chatter blockers are formed to be offset with respect to the diametric center line of the cutter.

The chatter blockers are positioned on the circle line and on the diametric center line of the cutter and have the shape of an aggressive rake or a hook to render the effect of pulling the bone so that vibrations and chattering can be reduced during cutting.

This chatter prevention technique plays a role of preventing the bone from being overcut.

Also, in order to easily remove the bone through cutting, the circumferential outer surface of the cutter head has the helix angle for facilitating the discharge of the chips when cutting the bone in a sideward direction.

At this time, if the helix angle is too large, the cutter becomes aggressive so that unwanted overcut of the bone can be caused.

Also, if the helix angle is too small, great cutting force is required so that the cutter is likely to be deformed and undercut of the bone can be caused.

Therefore, in the present invention, the helix angle is set to 10~20~ so that a cutting condition can be optimized when cutting uneven density bone.

Also, in order to remove the bone through cutting, since the cutter must be rotated at a high speed, the hardness of the material of the cutter must be in the range of HRC80•120.

If the hardness is not adequate, due to a chattering phenomenon during cutting, a portion of the bone which must be precisely cut is likely to be undercut or overcut. Thus, by selecting a material capable of ensuring excellent stiffness, the cutter is manufactured as to withstand all forces and vibrations so that defects are not caused in the bone.

Further, if a cutter having a large cutter head diameter is used as in the conventional art to increase VRR (volumetric removal rate), the cutting performance of the cutter can be improved. However, due to the large diameter of the cutter, an incision size increases, and the likelihood of the soft tissue and other important tissue to be extensively retracted increases, otherwise the soft tissue including the flesh is likely to be damaged.

In the present invention, due to the fact that a small-sized cantilevered cutter is used to permit partial cutting so that a cut surface has a reduced size, the cutting of the bone can be performed stably without requiring extensive retraction of the skin.

Besides, in the present invention, by using the cantilevered cutter having a minimum diameter and a maximum possible length, surgery can be performed even in a narrow space. In the present invention, the conventional approach for surgery, in which the cutter is moved only from the anterior side of the knee joint and the extensive retraction of tissue is caused when performing surgery, is discarded. Instead, in to the present invention, the distal end of the cutter is introduced medially or laterally not only from the anterior center part of the knee joint but also from the posterior center part of the knee joint without causing impingement between the cutter and surrounding tissue such that the path of the cutter is optimized, so that a space can be secured sufficiently, whereby it is not necessary to extensively retract the surrounding tissue.

Hereafter, the preferred embodiments of the present invention will be described with reference to the attached drawings.

FIGS. 1 through 29 are schematic views illustrating the respective cutting steps of a method for cutting the knee joint using a robot in accordance with one embodiment of the present invention.

First, the most important factor to be considered when cutting bone is to maximally prevent the impingement between a cutter and surrounding tissue. Therefore, in order to ensure safety when performing surgery, the cutter must be introduced in sideward directions from the anterior center part or the posterior center part of the knee joint so that no impingement is caused between the cutter and the patella which is pushed sideward after the incision of the skin.

Referring to FIG. 1, a cutter 10 performs ½ cutting for the medial aspect (when viewed from the Whiteside's line) of an W anterior chamfer in a parallel fashion to the Whiteside's line. At this time, a sleeve 14 for supporting the cutter 10 is positioned centrally on a surgery-receiving portion, and the distal end of the cutter 10 is pivoted medially just like drawing a semicircle while defining an angle in such a way as to form a tunnel. According to this, it is possible to solve the problems caused in the conventional art due to the fact that it is necessary to retract surrounding skin tissue as the cutting is conducted while the cutter sleeve is moved from the anterior side of the knee joint in such a way as to define a prescribed locus.

In the drawing, the reference character A designates an anterior aspect, M a medial aspect, P a posterior aspect, and L a lateral aspect.

This maneuver is done first in order to clear bone from the anterior aspect of the next plane to be cut which would be a distal surface plane.

The advantage of tunnel cutting is purely the fact that the bone left after cutting can safely protect the surrounding soft tissue from a cutter head 12 rotating at a high speed, that is, cutter edges. This means that the remnant bone T to be subsequently removed through additional cutting serves as a safety shield (a remnant bone cap) between the cutter 10 and the skin tissue. When cutting the bone, the more the thickness of the remnant bone T increases, the more the wavelength, at which the vibrations generated from the cutter 10 are transmitted to the skin tissue, decreases.

To this end, it is preferred that the cutting be conducted with the diameters of the cutter 10 and the cutter shaft 11 minimized.

The tunnel cutting is limited by the length of the cantilever of the cutter shaft 11, that is, the length of the free end portion of the cutter shaft 11 exposed out of the sleeve 14 for supporting the cutter shaft 11. A sufficient cantilever length is required to cut away all bony surfaces.

At this time, ideal would be a cantilever long enough to reach all extremities of the prescribed bony surface cuts, and the stiffness of the material of the cutter must be engineered to withstand all known forces and vibrations during cutting.

In the present invention, the diameter of the cutter 10 depending upon the length of the cantilever is engineered based on the fact that the diameter is proportional to a maximum cantilever length. In order to prevent the cutter edges from cutting away more of the bony surface safety shield and causing damage to the surrounding soft tissue, the smallest possible cutter shaft diameter is idyllic.

Figure 2:
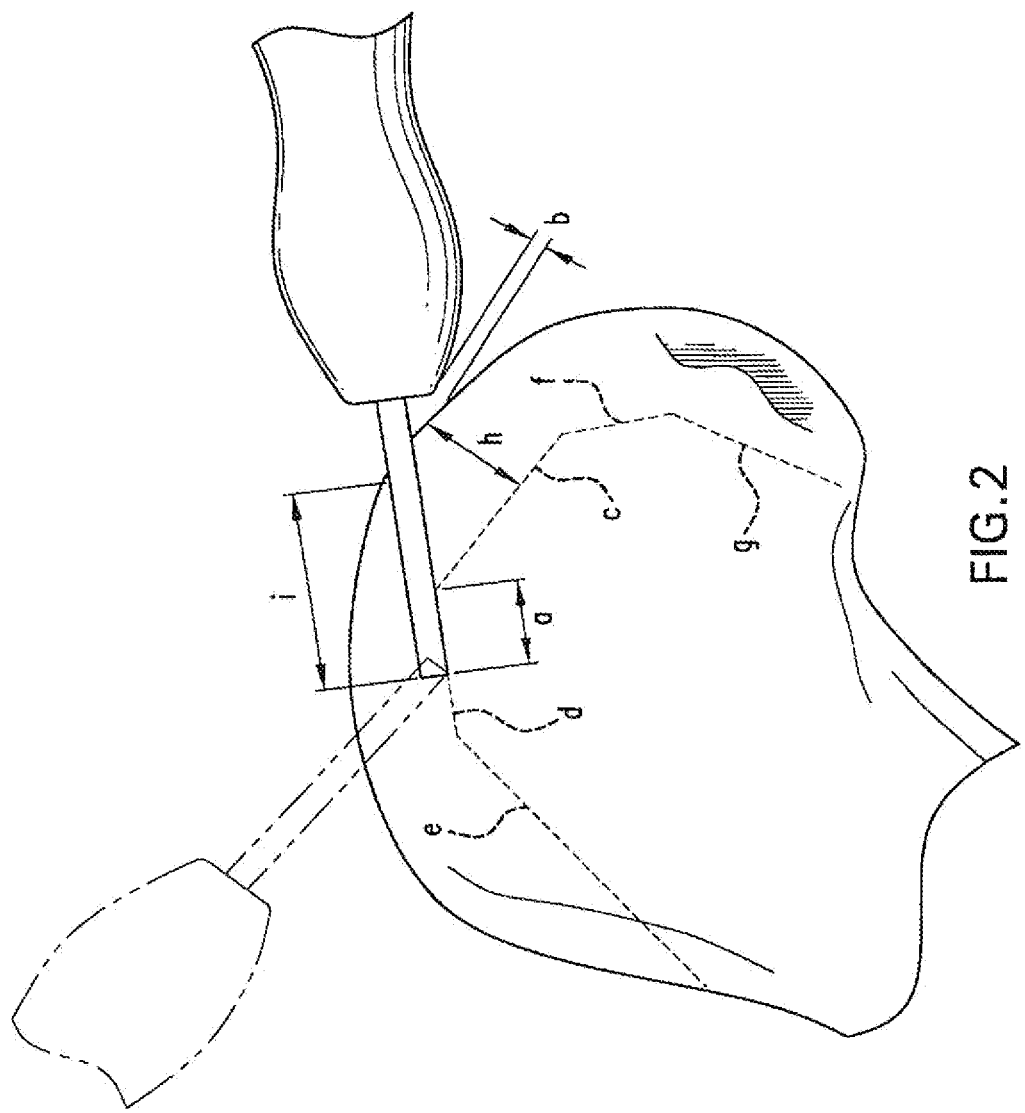

To this end, in the present invention, as shown in FIG. 2, a cutter has a diameter of 2~3 mm and a sufficient cantilever length 'i' for respective planes to be cut through partial cutting. Here, the cutter having the diameter and the cantilever length is engineered in the shape of a cantilever which is sufficiently long as to cut prescribed bony surfaces 'c', 'd', 'e', 'f' and 'g'.

In the drawing, the reference character 'a' designates a part of a bony surface to be removed on the anterior chamfer when performing cutting using the cantilever length according to the present invention, and the reference character 'b' indicates that the sleeve 14 is separated from the upper bone of the knee joint by a prescribed distance.

Figure 3:
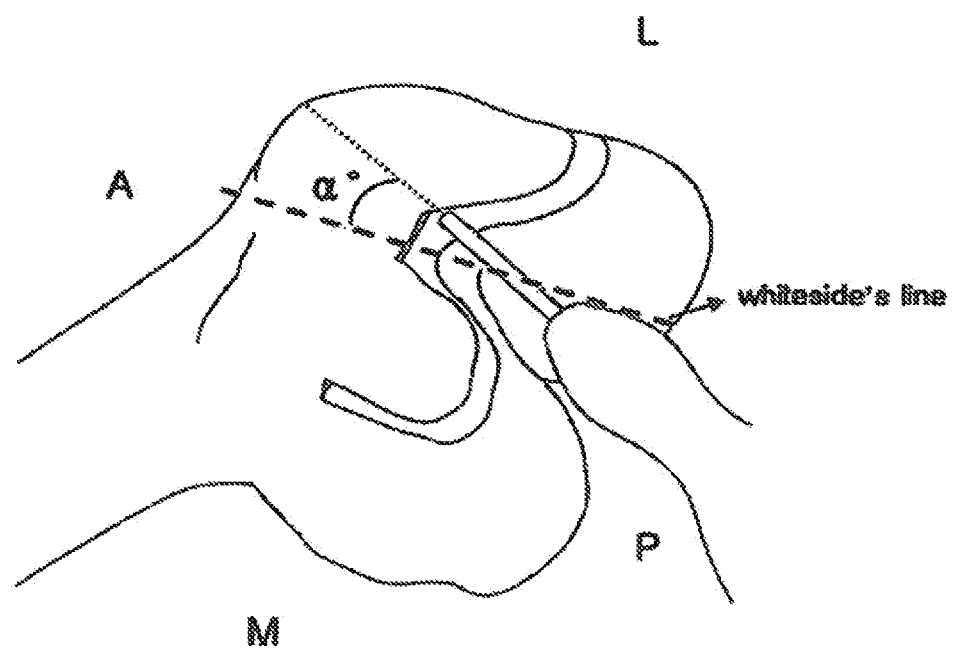

As shown in FIG. 3, a second cutting sequence is conducted such that the distal end of the cutter is moved by slanting it medially just like drawing a semicircle to prevent impingement of the cutter upon the patella and a supporting patella ligament structure which are positioned on the lateral aspect L on the drawing.

According to this, since the sleeve 14 is not substantially moved in a sideward direction, the impingement of the cutter upon the patella and other tissue is not caused. Also, a skin incision area upon initially conducting surgery can be minimized, and it is not necessary to retract the skin when cutting the bone.

In order to minimize patella subluxation, a prescribed angle α° slanted medially in reference to the Whiteside's line is optimal to perform the cutting of the lateral aspect of the ½ anterior chamfer surface cut plane.

At this time, the slant medially prevents the cutter 10 and the cutter holding sleeve 14 from impinging upon the patella and the surrounding soft tissue.

A small incision would restrict the subluxation of the patella, and therefore this novel approach is idyllic.

Perhaps slight elevation is adequate but not necessary because this invention of tunnel cutting creates a safety shield bone cap that is present between the rotary cutter and the soft tissue. A small diameter cutter aids in maximizing the thickness of the remnant bone, creating a stronger safety shield.

Figure 4:
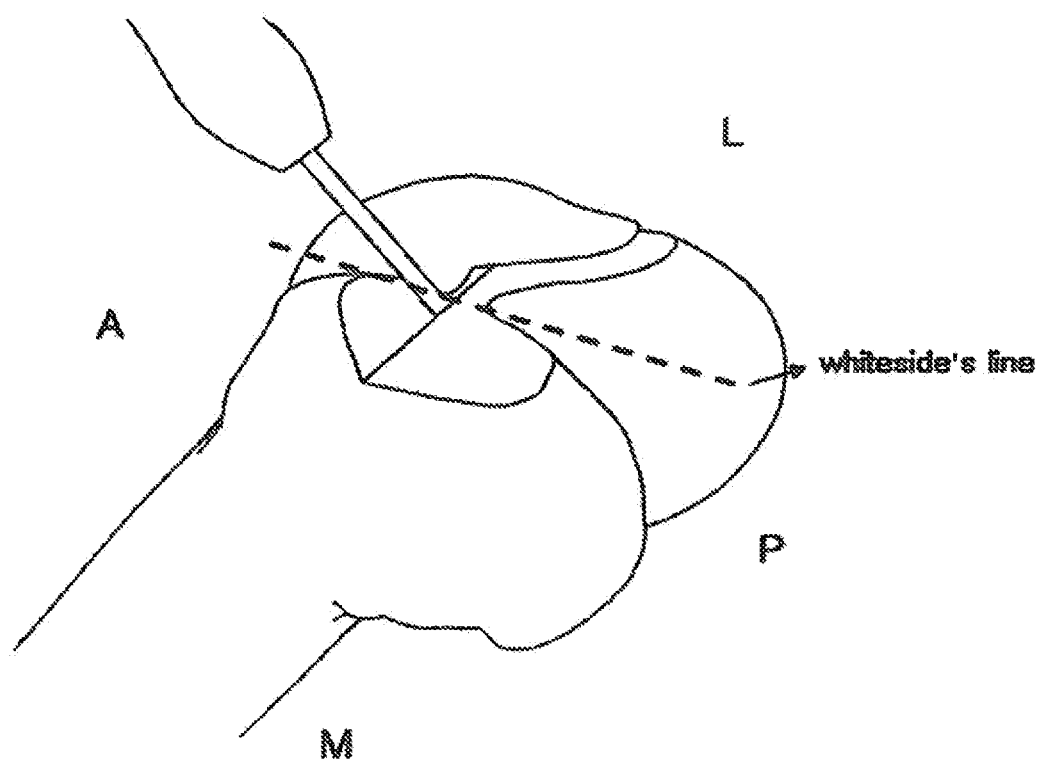

As shown in FIG. 4, after completing the ½ cutting of the medial and lateral aspects of the anterior chamfer, the cutter is reoriented at an orientation parallel to the floor and cuts though just enough as to remove the remnant bony surface on top of the anterior chamfer cut surface.

The principle behind this maneuver is to clear the bone to perform a distal surface tunnel path.

The principle behind the tunnel path is to prevent the cutter tip from protruding and causing any soft tissue damage.

This method of reshaping bone has proven to completely eliminate the need for extensive soft tissue retraction, prevent patella subluxation, and facilitate the preservation of all surrounding soft tissue.

Due to the fact that there is always a bony surface between the cutter tip and the caved soft tissue, the safety of high speed tunnel cutting for bone shaping becomes evident.

Figure 5:
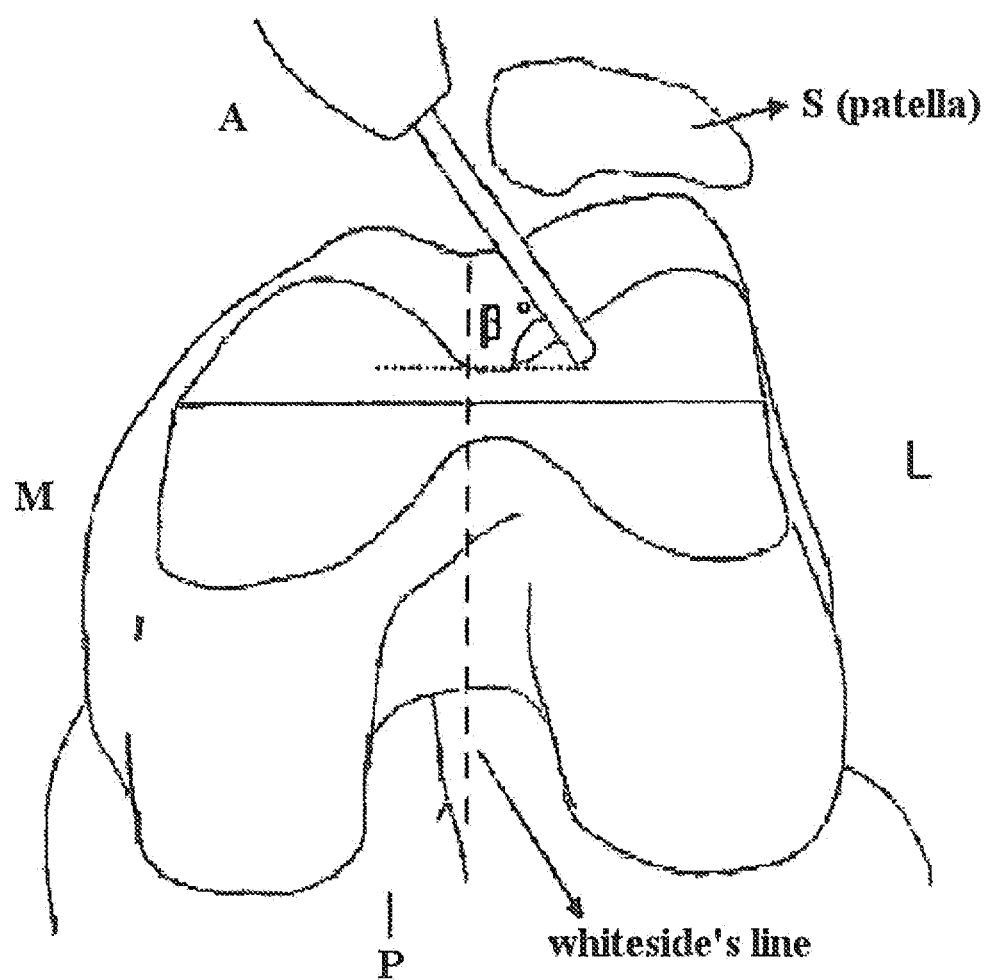

As shown in FIG. 5, the lateral aspect of the remnant bone hovering above the anterior chamfer surface is removed by a novel new bone clearing pass. In order to prevent the subluxation of the patella and its ligament structure to avoid their being in the way of the cutter, a direction change is prescribed slanted medially with a prescribed angle β°.

This eliminates the need to displace the patella and its supporting structure to perform the lateral aspect cutting of the ½ anterior chamfer bone clearing cut.

The intent of this maneuver is to avoid any injury by way of stretching, tearing and impinging of any surrounding tissue by the cutter, and therefore deoxygenating of any surrounding tissue that currently all prior art surgical techniques involving a limited incision introduce and is a well known side effect of limited incision surgery.

Increased stretching, tearing, impinging and shearing of vital and surrounding soft tissue are side effects of a surgical technique that is done using prior art methods with larger diameter heads to increase a VVR (volumetric removal rate).

Figure 6:
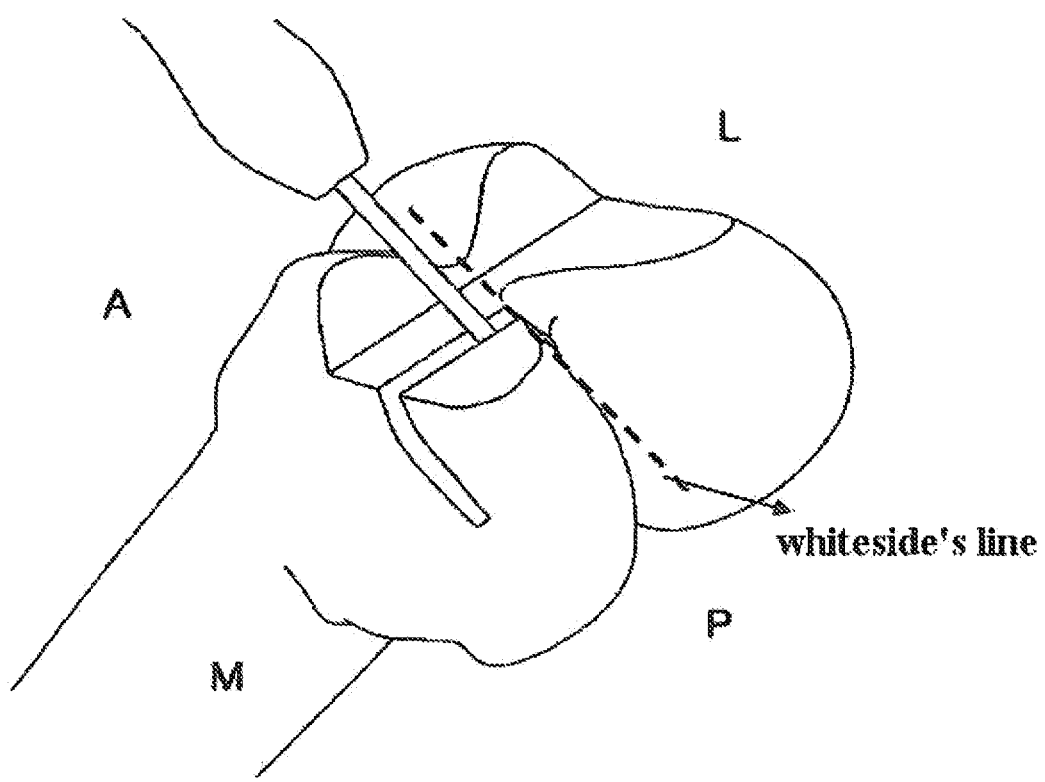

Next, as shown in FIG. 6, the medial aspect of the distal surface cut plane is done parallel to the Whiteside's line.

The slender cutter with a stiff shaft capable of handling all vibrations associated with uneven density bone milling is the key component as to keep the cutter head sandwiched between bony surfaces.

A cutting sequence together with a cutter shaft design of this nature is proven to prevent the cutter head from grazing caved-in soft tissue that has not been lightly elevated, eliminating the need for extensive soft tissue retraction.

The distal surface is overcut posterior.

This maneuver is to make it easier for the surgeon to crack away the bony surface with a standard orthopedic chisel. This method of overcutting posterior has no complications as the prescribed thickness of the bony surface cap is on average 9 mm thick.

The slim nature of the cutter design allows that the cutter remains encapsulated in the bone and ensures that there is the bony cap acting as a kind of safety shield between the cutter head and the soft tissue at all time while the cutter in milling. Therefore, this method and the system used promote a tissue sparing technique by eliminating the need for tissue retraction.

Figure 7:
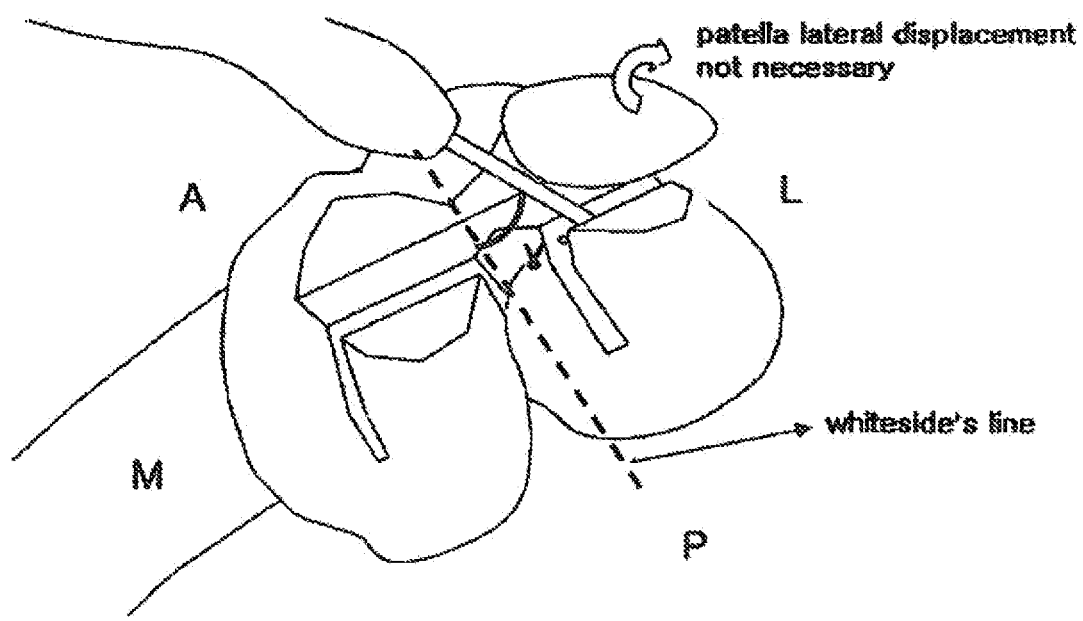

Then, as shown in FIG. 7, lateral aspect of the distal cut is then cut out.

In order to preserve the original position of the patella and its supporting tissue, the end effecter is prescribed an angle of γ° slanted medially.

Since the patella and the supporting tissue are not displaced laterally, no soft tissue trauma or abrasion is assured. The fact that there is the bony cap sandwiched between the rotary cutter head and soft tissue makes this method and system a new and novel approach to bone milling technology. Therefore, as the bony cap prevents the cutter from adversely influencing the surrounding soft tissue by serving as the safety shield, the safety of the surgery is enhanced fully.

Figure 8:
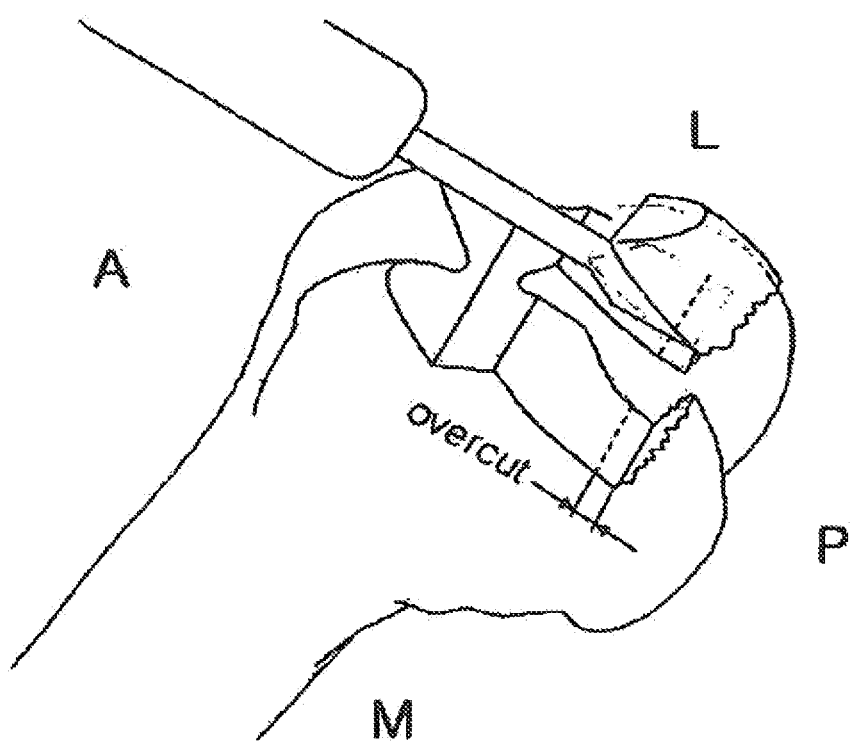

As shown in FIG. 8, after the medial and lateral aspects of the distal surface cut are complete, the remnant safety cap (the cutter safety shield) can be easily broken off using the chisel being a tool similar to a driver.

This maneuver is simplified by the slight posterior overcutting. The bony material safety shield is snapped off clearing a path for the next phase of the cutting sequence.

As seen in the illustration, the dotted line is the edge of the most posterior point of the distal surface of the implant.

The chisel pivot point is allowed to rest past the important distal surface and a pivoting action that is not on the surface area that the implant would lie on is an idyllic way to snap off the bone safety shield. Any damage to the bone from the chisel point is outside the surface that is to be used for implant to bony surface contact. Therefore, the precisely cut surface can be obtained and, when the implant is inserted thereafter, the implant can precisely match the cut surface of the bone.

Figure 9:
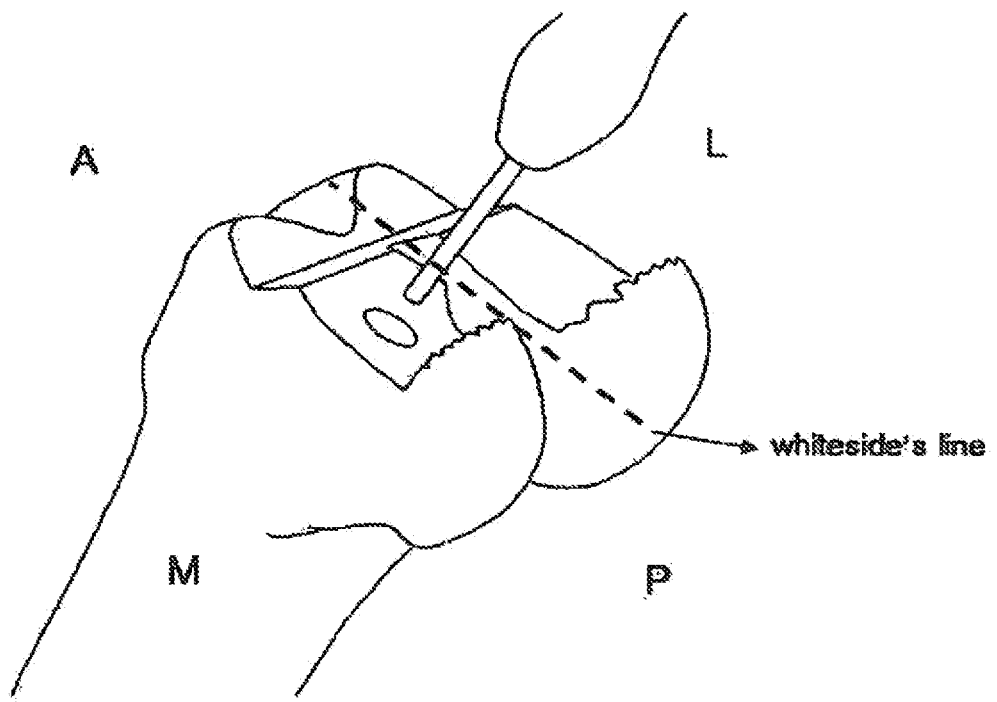

Next, as shown in FIG. 9, a medial distal post hole is defined in a circular motion using the same cantilever cutter.

Figure 10:
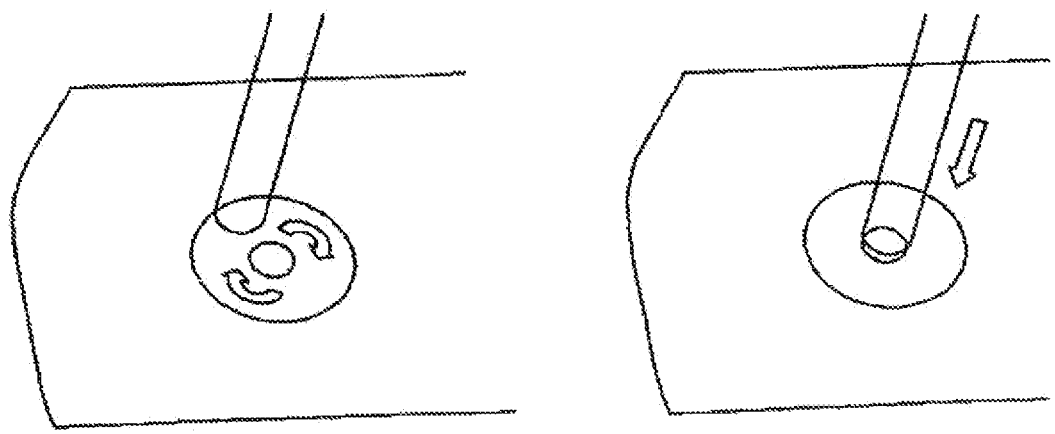

Namely, as shown in FIG. 10, due to the minute nature of the cutter, an island is left in the center of the cut which is then cleared away by a direct pass down the center of the island of bone remnant.

Figure 11:
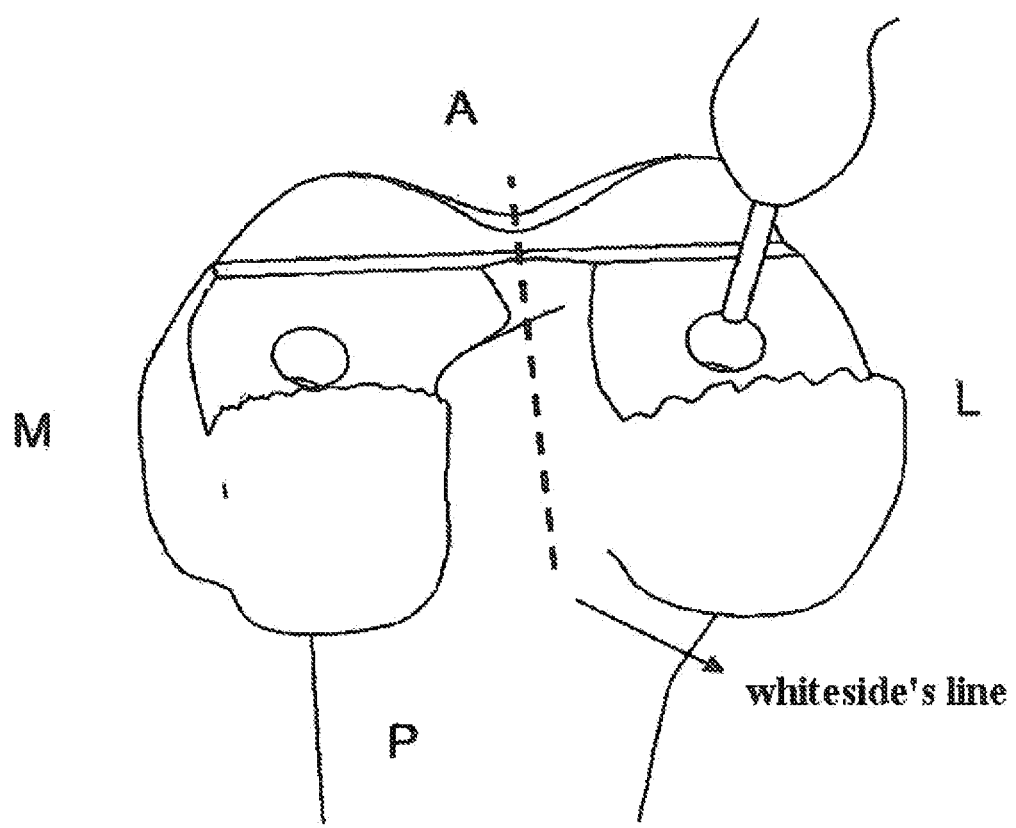

Referring to FIG. 11, a lateral distal post hole is defined in the same fashion, a series of circular moves cut out the prescribed diameter leaving an island of the bony structure in the center. This is immediately removed by a single pass directed down the center of the post.

Figure 12:
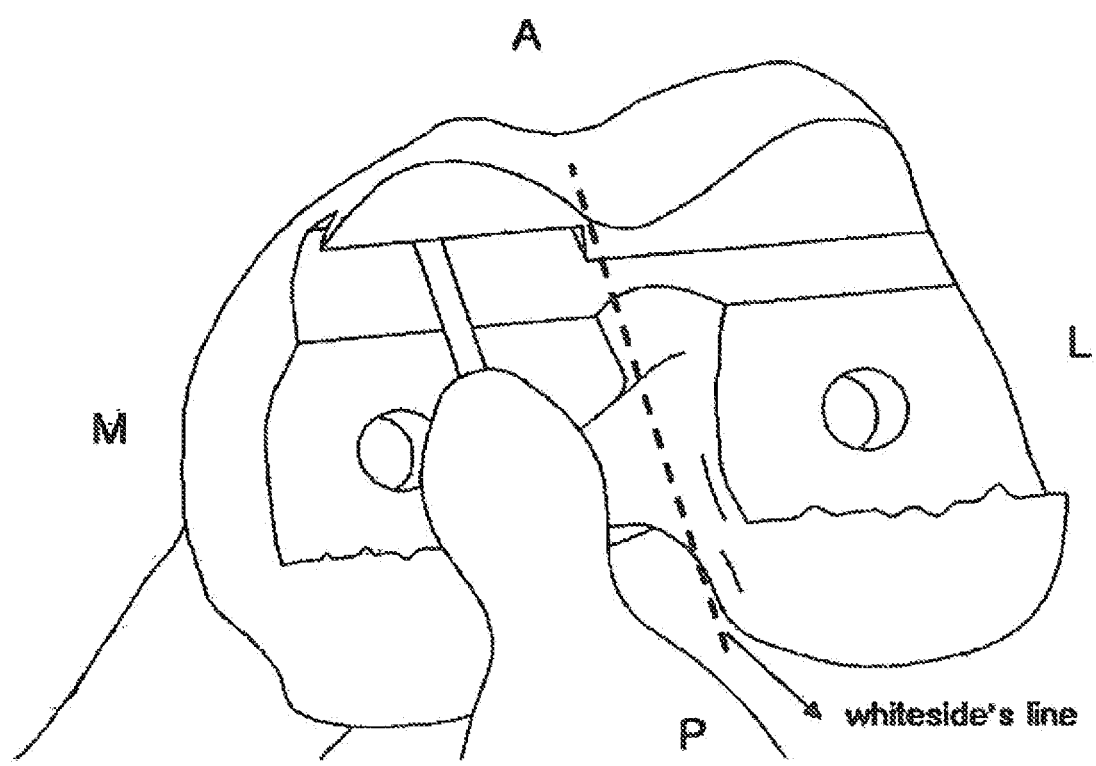

As shown in FIG. 12, the cutting of the medial aspect of the anterior chamfer is conducted parallel to the Whiteside's line.

At this time, since the bony cap is left between the cutter and the soft tissue, the surgeon can perform surgery while feeling safety, and due to this fact, it is not necessary to retract the surrounding skin tissue to define a space.

In other words, the cutter can easily reach the medial aspect of the anterior chamfer without retracting the surrounding tissue or further exposing the surgery-receiving portion.

To this end, the cantilevered cutter according to the present invention, which has a small diameter and a sufficient length, can leave a substantial amount of bone between the edges of the cutter head and the soft tissue to serve as the safety shield.

At this time, because the bone existing on the distal surface has already been removed, the length of the cantilever for cutting the anterior chamfer becomes sufficient.

In the cutting procedure according to the present invention, while it is important which surface is to be first cut, it is very important that a space is created by removing the bone such that the bone can be properly cut using the cutter having the small diameter and the prescribed length of the cantilever.

Figure 13:
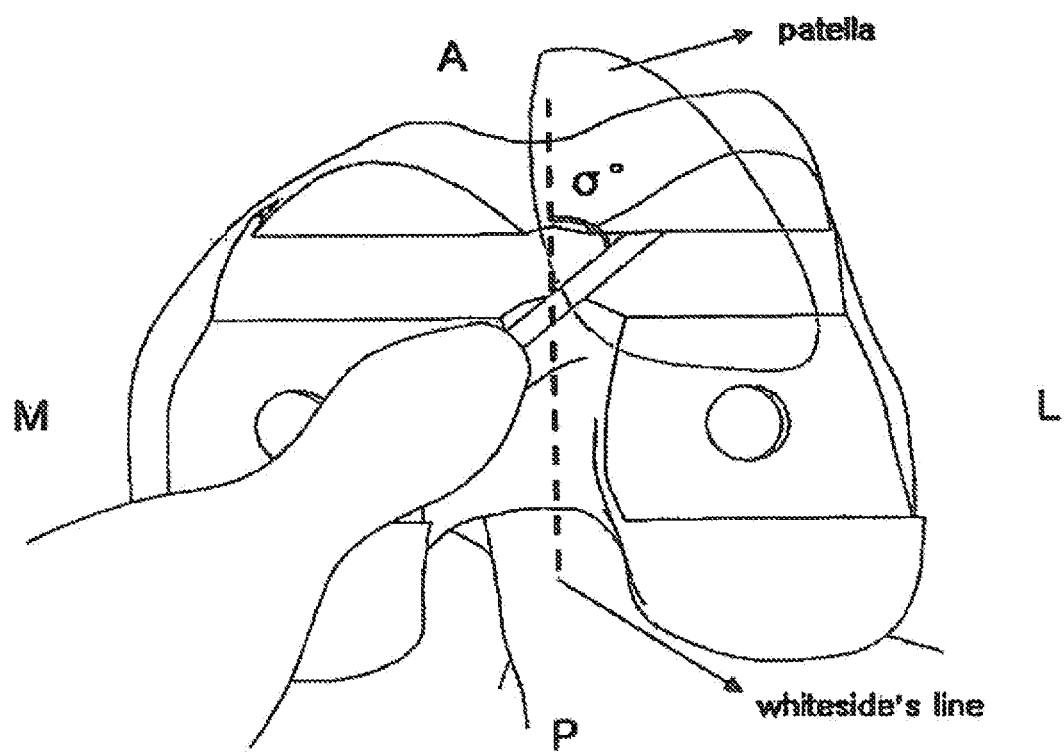

As shown in FIG. 13, the lateral aspect of the anterior chamfer is cut by slanting the cutter by a prescribed angle of σ°.

The principle behind this maneuver is to prevent the cutter and the sleeve from impinging upon the tissue during cutting so that the cutting can be conducted in an appropriate way.

Further, an advantage is conferred in that a maximum amount of bone can be left through the tunnel cutting, and an effect is conferred in that the damage to the soft tissue and the retraction of the soft tissue can be minimized.

Figure 14:
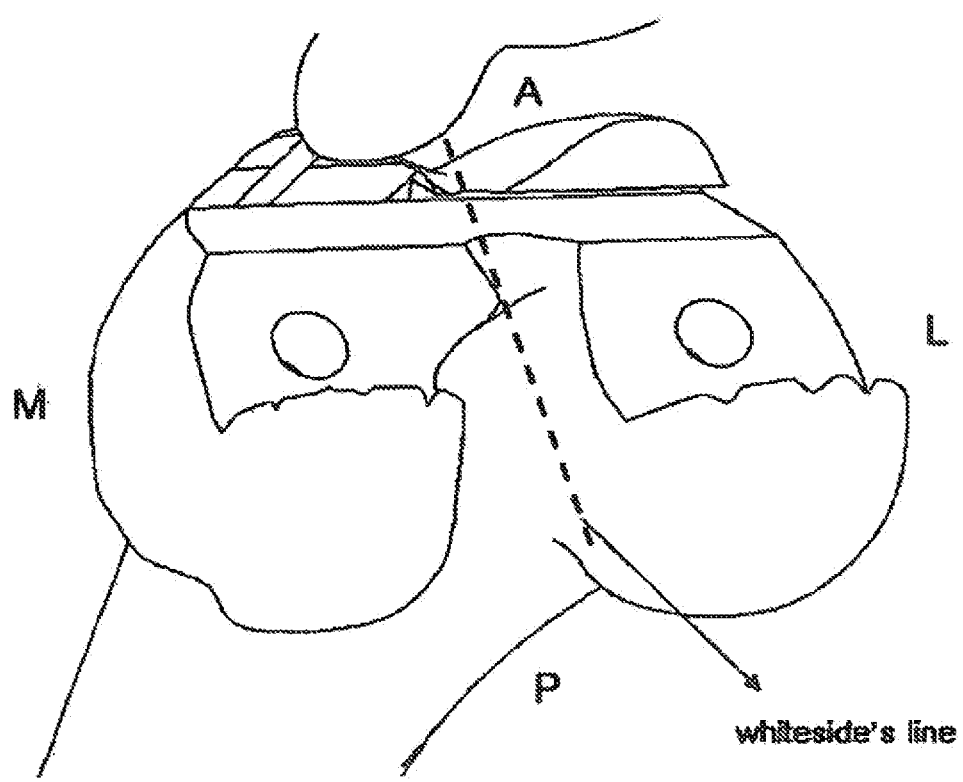

As shown in FIG. 14, by moving the cutter from the Whiteside's line in the medial direction, the ½ cutting of the medial aspect of the anterior chamfer is conducted parallel to the Whiteside's line.

Also, in this procedure, the sleeve is positioned centrally on the surgery-receiving portion, and the distal end of the cutter is pivoted medially just like drawing a semicircle so that cutting is conducted. The tunneling cutting is implemented using the cutter having the small diameter. It is not necessary to retract the skin or the supra patella pouch.

Namely, as the impingement of the cutter upon the surrounding tissue is maximally prevented so that the influence of the surgery is not exerted to the surrounding tissue, the patient can be prevented from swelling, can feel reduced pain, and can be recovered quickly.

The supra patella pouch includes the soft tissue facing the patella ligament, the blood supply, and the synovium. The impingement of the cutter upon the supra patella pouch may double the swelling and the pain and decrease the surgery satisfaction degree of the patient.

The present invention prevents the impingement of the cutter upon the supra patella pouch and satisfies all conditions therefor.

Figure 15:
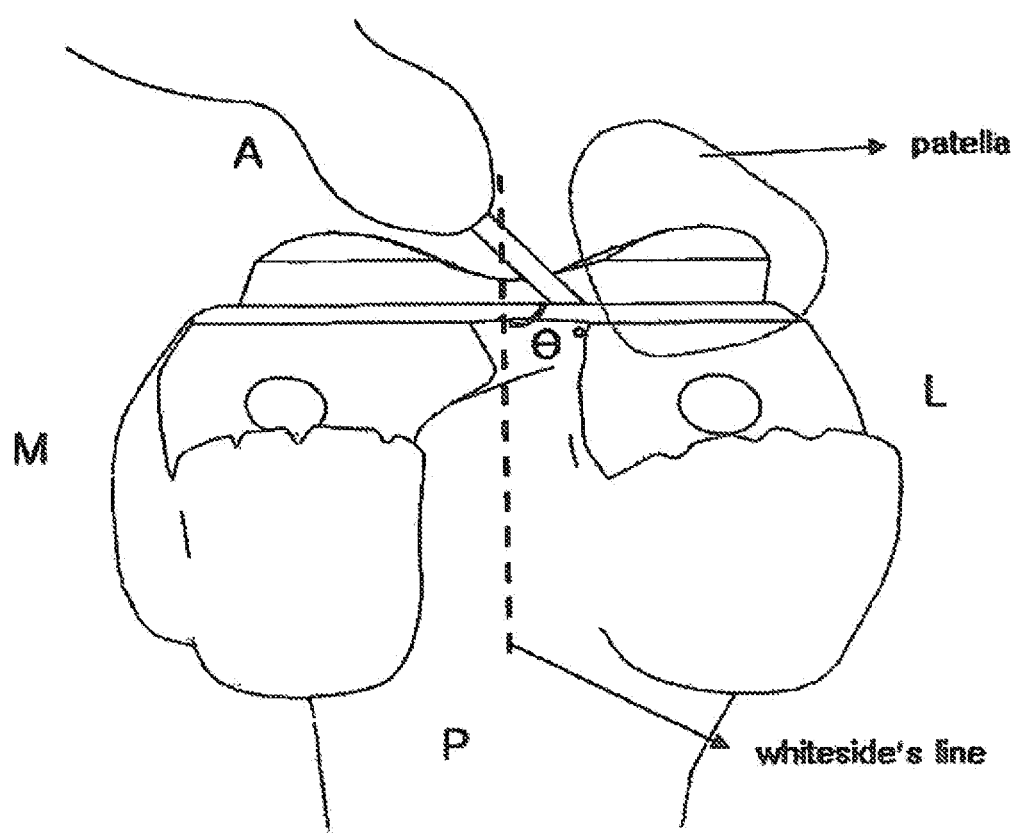

To this end, as shown in FIG. 15, by moving the cutter from the Whiteside's line in the lateral direction by slanting the cutter by a prescribed angle of θ° with respect to the Whiteside's line, the ½ cutting of the lateral aspect of the anterior chamfer is conducted.

At this time, since the sleeve is positioned centrally adjacent to the Whiteside's line, any impingement does not occur. Also, since the tunnel cutting is conducted to leave the bony cap serving as the safety shield, the cutter is prevented from impinging upon the supra patella pouch.

Figure 16:
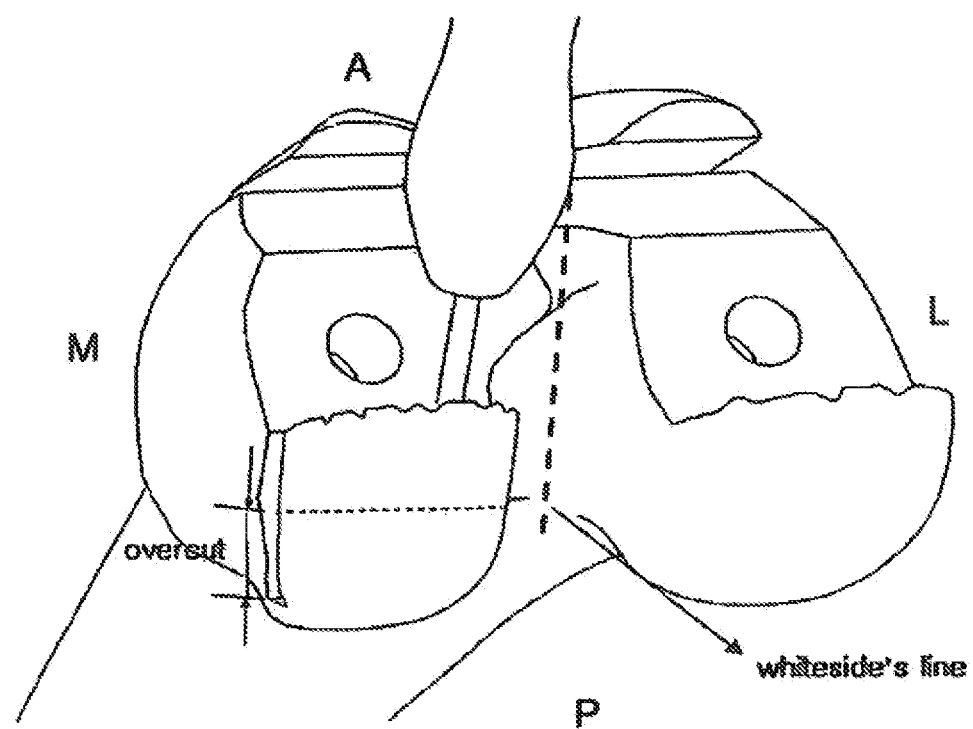

As shown in FIG. 16, the cutting of medial aspect of the posterior chamfer cut is performed parallel to the Whiteside's line and in a direction anterior to posterior.

A diamond shape over the medial condyle formed naturally by the soft tissue is the natural unrestricted seating position of the soft tissue after incision.

This invention facilitates the method that entails a maneuver in the anterior to posterior direction to resect the posterior chamfer surface.

By doing so parallel to the Whiteside's line and approaching directly at the level of the prescribed plane, it is simply possible to tunnel the chamfer without retraction, and slight elevation may be necessary. The overcut is then introduced as to aid in the easy removal of the bony structure safety shield using the chisel.

Figure 17:
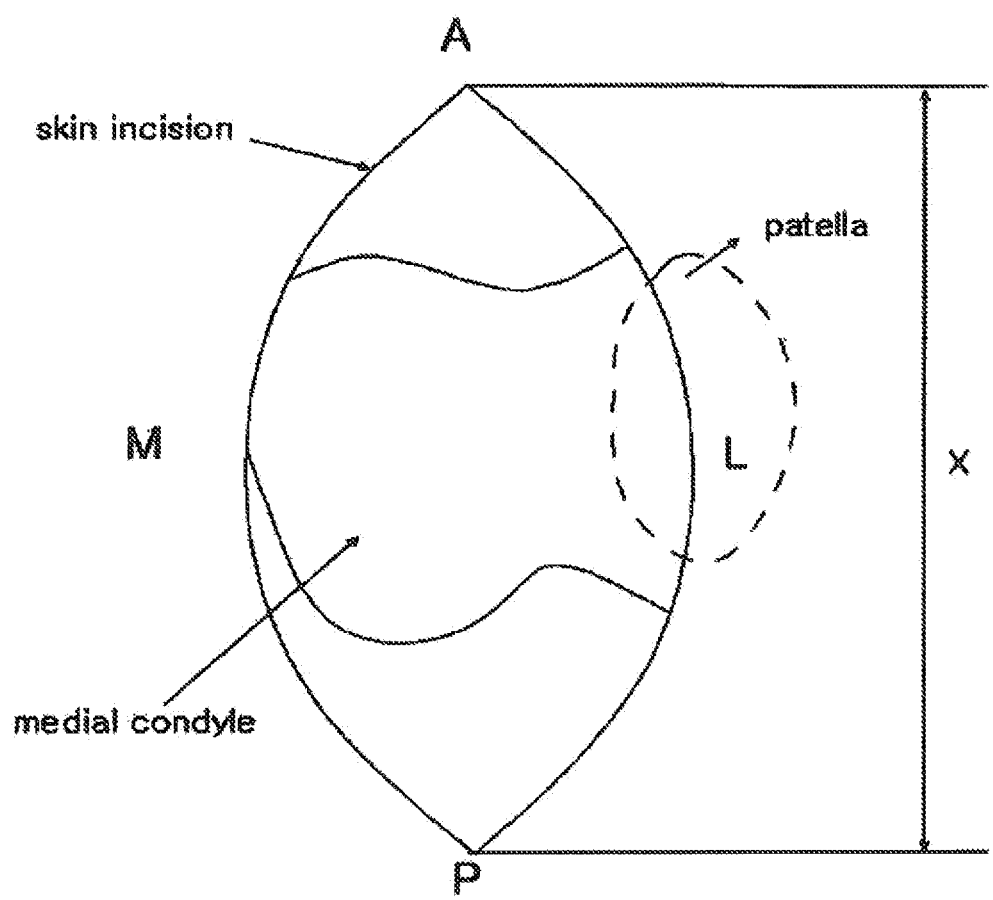

As shown in FIG. 17, because the cutter according to the present invention conducts cutting while guiding the distal end thereof from the center toward the sides of the surgery-receiving portion, the impingement between the cutter and all associated tissue does not occur, and therefore, the tissue can be efficiently protected even in a special chamfer cut.

Figure 18:
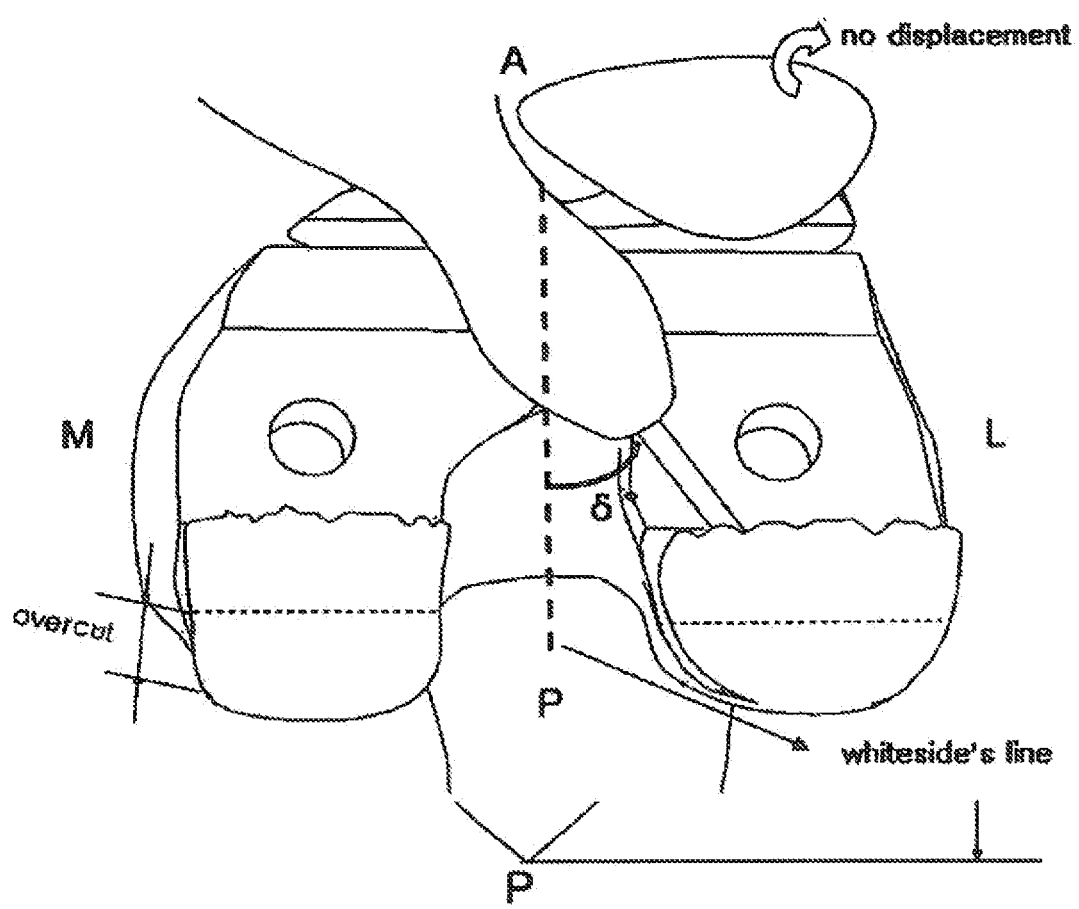

As shown in FIG. 18, the lateral aspect of the posterior chamfer plane cut is performed with the cutter slanted medially by a prescribed angle of δ°.

This novel maneuver is performed as to prevent the sleeve and the cutter from impinging upon the surrounding soft tissue and the patella.

The novelty behind this is that the surgeon is now able to cut out the lateral aspect of the posterior chamfer without retracting the patella or the surrounding soft tissue. The natural unrestricted seating position of the soft tissue even with an incision side considered minimal invasive is adequate.

Figure 19:
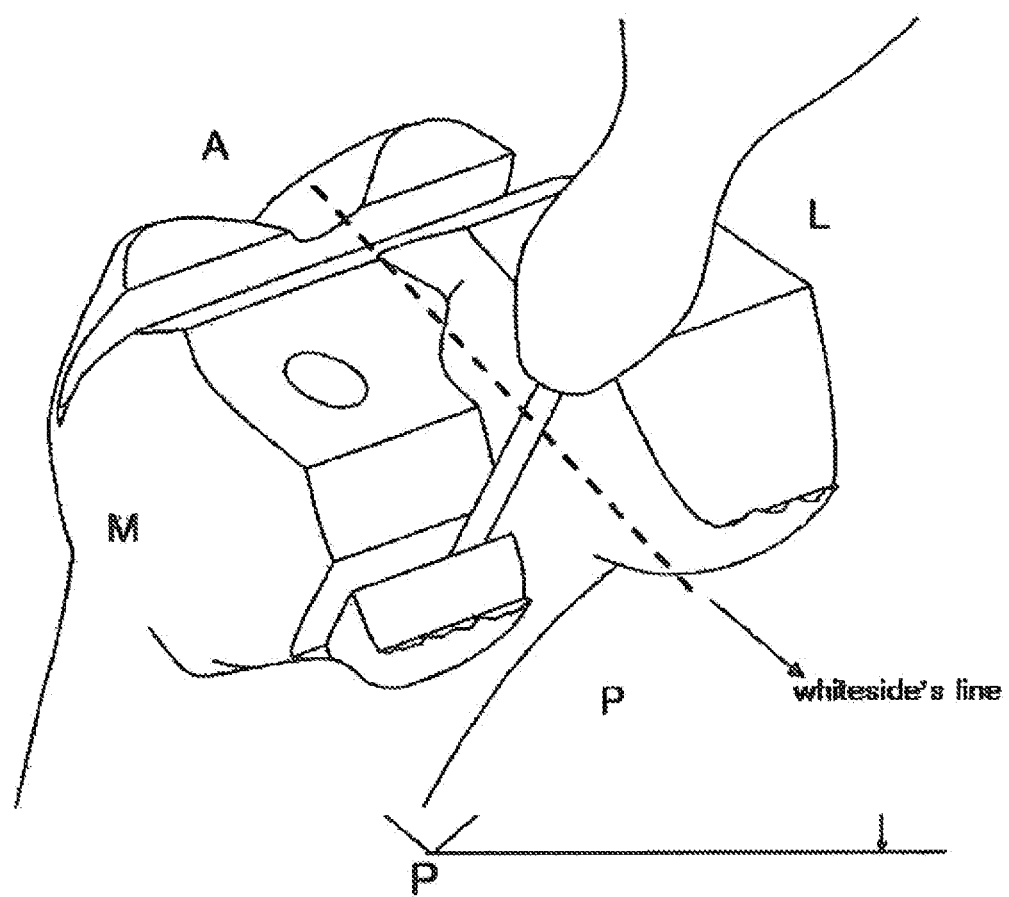

As shown in FIG. 19, the cutting of the medial aspect of posterior condyle is performed parallel to the axis of the bone or perpendicular to the distal surface.

This maneuver is easily done after a diamond shape is formed by the soft tissue incision as can be seen from the medial direction.

The novel tunneling cutting concept of the present invention is most highlighted in the cutting of the medial and lateral aspects of the posterior condyle.

That is to say, the cutter of the present invention remains encapsulated in the bone and ensures that there is the bony cap acting as a kind of safety shield between the cutter head and the soft tissue at all time while the cutter in milling, so that the likelihood of the cutter to damage the soft tissue around the posterior condyle, nerves and the membrane covering the artery is minimized. Therefore, by performing the cutting operation using the cutter having the small diameter and the small size, it is possible to prevent the loss of a substantial amount of bone, and due to this fact, a most significant advantage is conferred in that the safety shield bony cap can be formed to have a substantial thickness so that the anterior membrane portion can be protected from the cutter tip.

Therefore, since safety is elevated and the high speed milling can be performed precisely within a narrow space, the stability of the surgery can be maximized.

Figure 20:
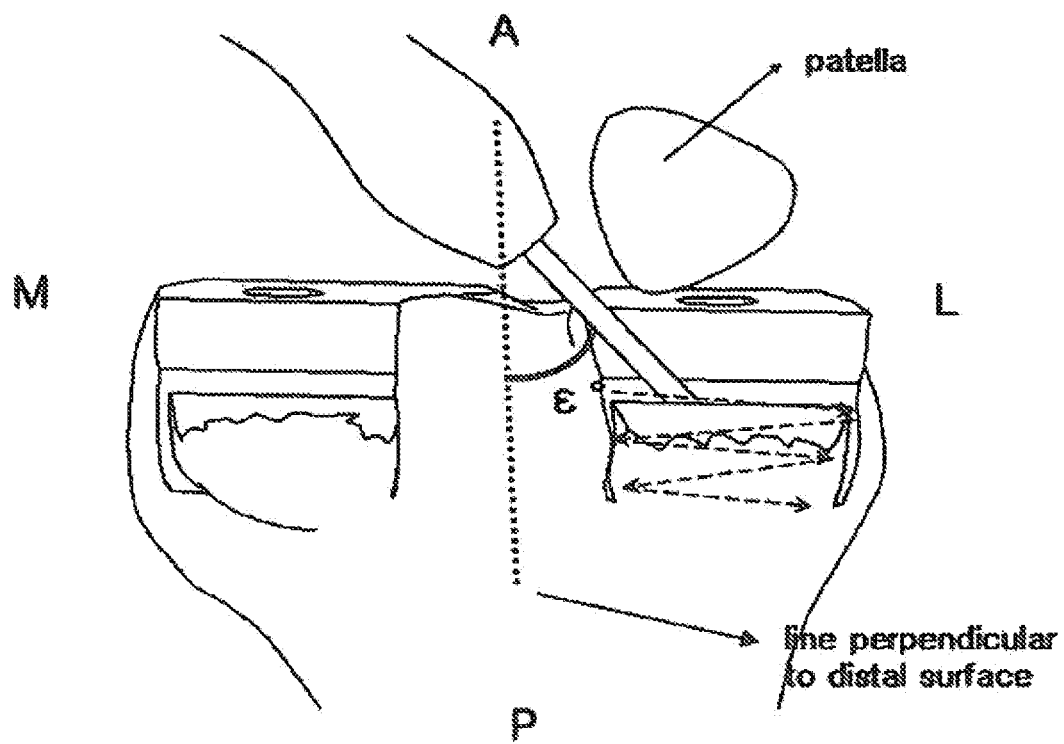

Referring to FIG. 20, the cutting of the lateral aspect of the posterior condyle is performed laterally at a prescribed angle of ε°.

In this maneuver, since the cutting is performed by slanting the cutter by the prescribed angle so that the cutter can cut the lateral aspect up to its extremity, it is not necessary to separately move the patella to secure a space.

Also, because the cutter having the small diameter is used to cut the bone, the bony cap serving as the safety shield can be left to protect the surrounding membrane tissue from being damaged.

Accordingly, the cutter can ensure remarkably increased safety when compared to the conventional milling cutter.

Figure 21:
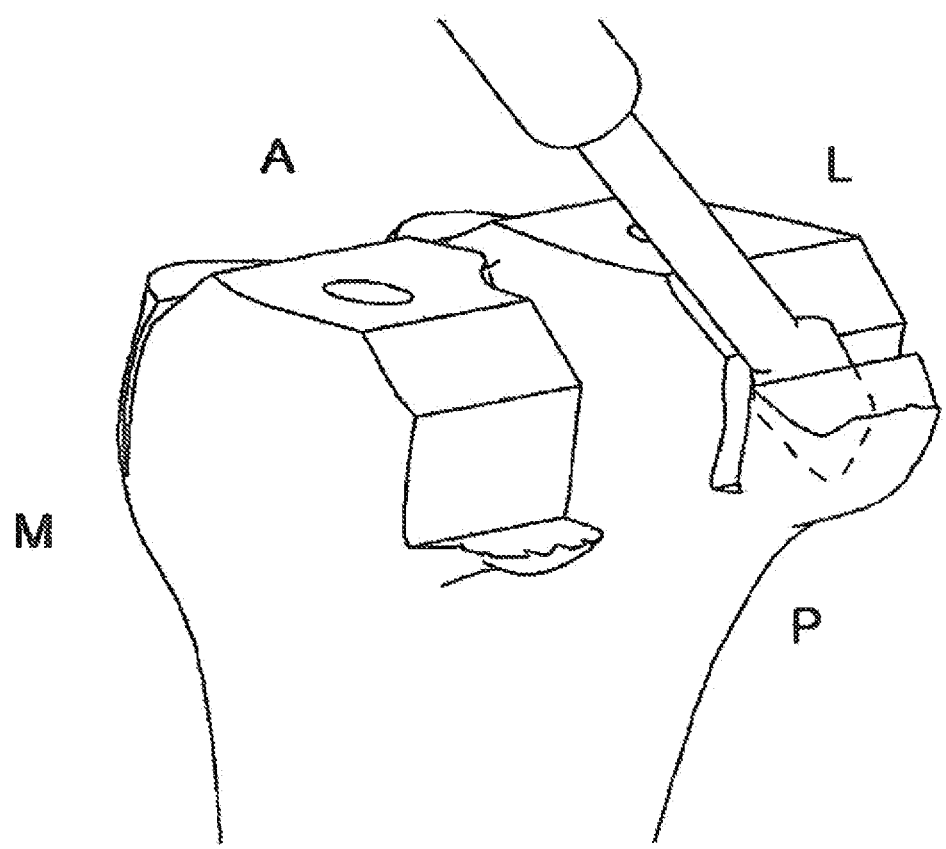

Referring to FIG. 21, the bony cap which is left to serve as the safety shield is easily removed using the chisel as the general surgical instrument for orthopedic surgery. That is to say, by inserting the chisel into the cut space and applying external force to the chisel, the bony cap can be easily removed.

As described above, in the tunnel cutting technique according to the present invention, in which a plane cut is formed by moving the cutter having the minimum diameter from the center toward the sides of the surgery-receiving portion and then the left bony cap is removed using a tool such as the chisel, the thickness of the bony cap can be set to be greater when initially cutting the bone using the cutter such that the bony cap can serve as the safety shield for preventing impingement between the cutter and the surrounding soft tissue and minimize the influence of the vibrations generated by the cutter, whereby the stability of surgery can be maximized.

Figure 22:
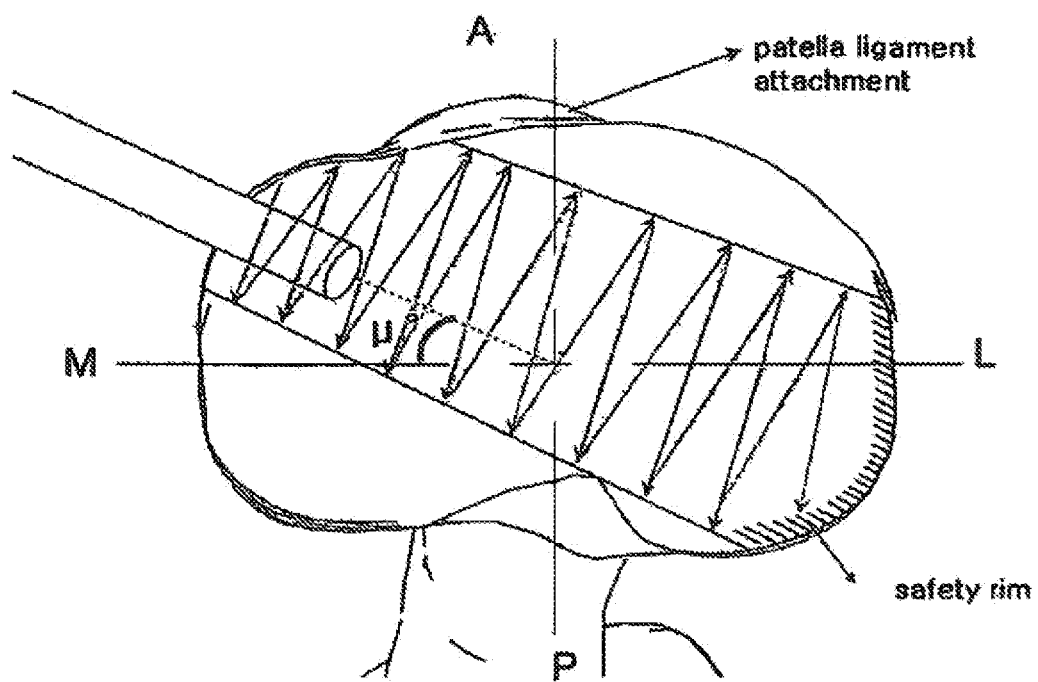

After the cutting of the upper bone of the knee joint is completed in the above-described way, the cutting of the lower bone of the knee joint is performed as shown in FIG. 22.

Since the upper surface of the lower bone of the knee joint is wide, the cutter, which is used to cut the upper bone of the knee joint and has the cantilever length of 20~30 mm and the diameter of 1.5~4.0 mm, is not used, and instead, a cutter, which has a cantilever length of 70~80 mm and a diameter of 4.0~6.0 mm, is used for quick cutting.

In other words, by using the large cantilevered cutter, planar cutting can be quickly performed with no slanting angle.

To this end, the cutter having the large diameter is introduced from the anterior position of the knee joint toward the medial-lateral line (the M-L line) with a slope of $\mu°$. At this time, the introducing direction of the cutter is optimized in the range of 15~30° with respect to the medial and lateral line.

This maneuver is to avoid any injury by way of stretching, tearing and impinging of the patella ligament which can be caused due to the minimal invasive surgery.

The cutting by the cutter is performed such that a safety rim for preventing the unwanted damage to soft tissue is left on the edge of the inward end of the bone, that is, on the lateral edge of the lower patella.

The reason why the safety rim is left is to prevent soft tissue behind the rear surface of the patella from being damaged by the cutter and to increase the safety factor in the bone cutting technique.

After the upper end center portion of the lower bone of the knee joint is partially cut in this way, the medial posterior portion is cut.

Figure 23:
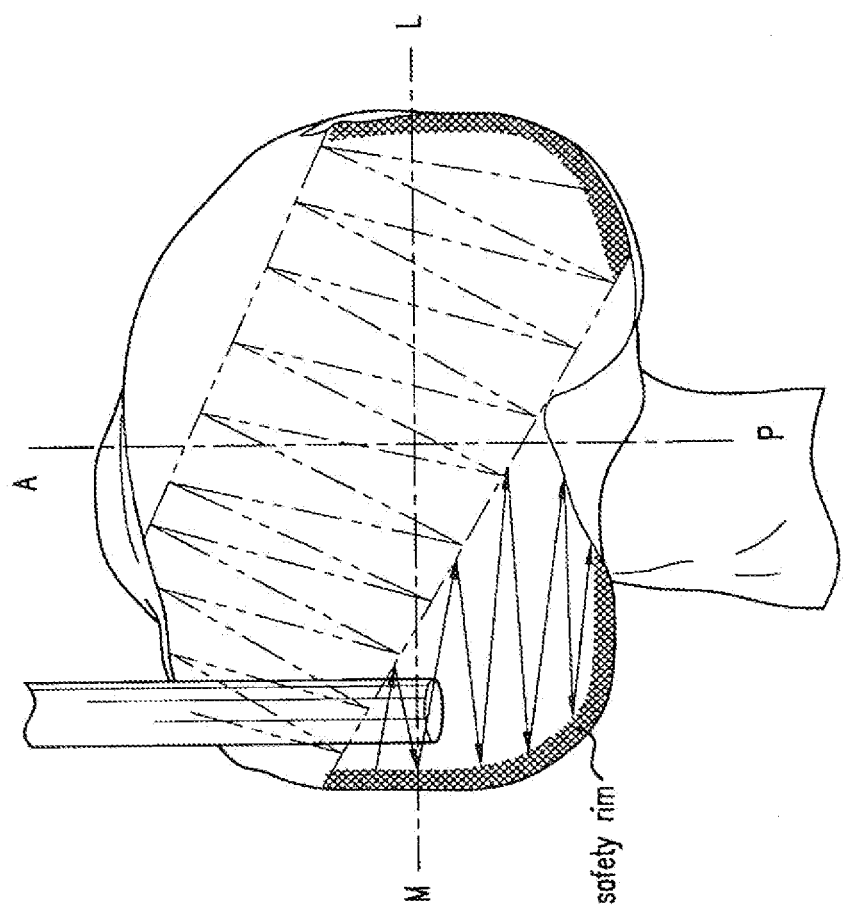

Referring to FIG. 23, the cutting of the medial posterior portion of the lower bone of the knee joint is performed by placing the cutter parallel to the anterior-posterior line (the A-P line) and then moving the cutter in a zigzag pattern to leave a posterior safety rim. By this maneuver, the safety rim can be formed on the posterior edge of the bone to prevent the abrasion of surrounding soft tissue and the anterior membrane.

The bone left in these ways can be easily removed using a small chisel, a micro saw, or a tweezers-shaped cutting implement.

Figure 24:
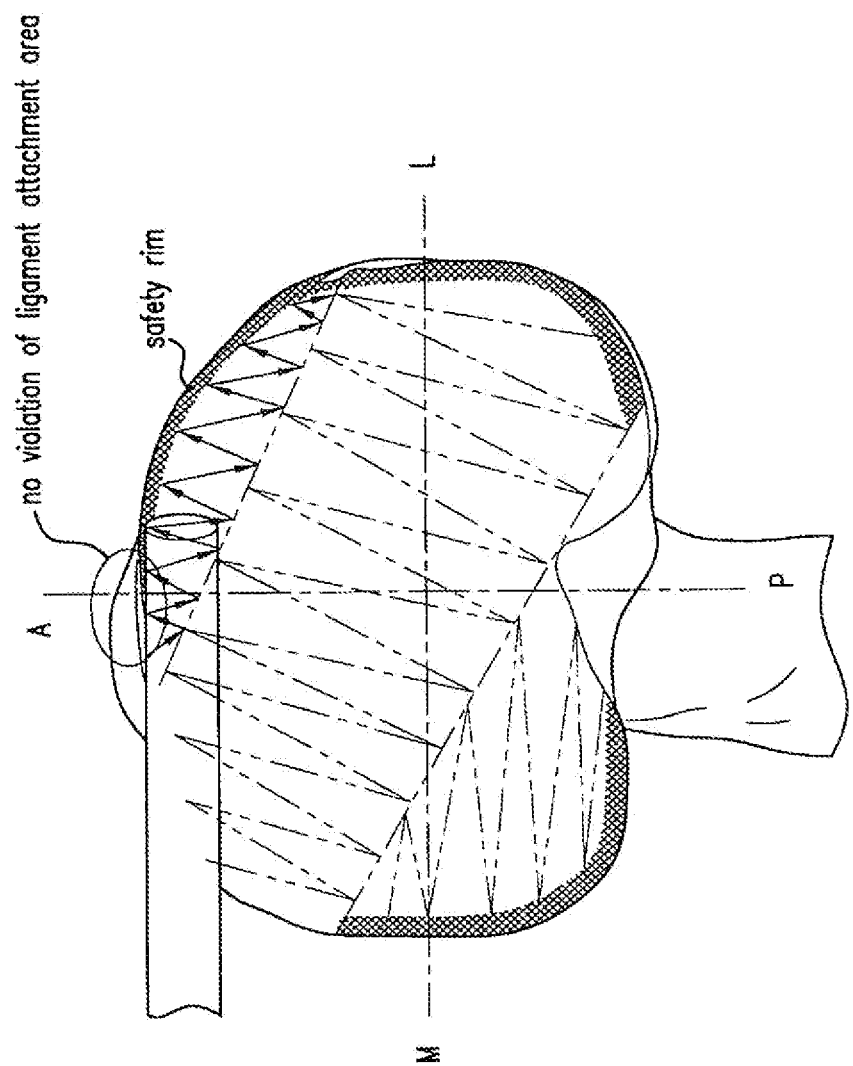

Referring to FIG. 24, the cutting of the lateral anterior portion of the lower bone of the knee joint is performed by moving the cutter in a zigzag pattern from anterior to lateral to leave an anterior safety rim.

In this maneuver, the cutter is placed parallel to the medial-lateral line (the M-L line) as can be readily seen from the drawing.

The safety rim formed as described above serves as a safety shield to prevent the soft tissue from being abraded (a phenomenon in which materials are gradually worn out when two surfaces brought into contact with each other are applied with force and are moved while slipping on each other). By leaving the safety rim having a small thickness, the cutter tip is prevented from damaging the patella and the supporting ligament structure, whereby the minimal invasive surgery can be further enabled. Also, when the surgeon cuts the lower bone, the surgeon can be convinced of surgical stability due to the presence of the safety shield.

Figure 25:
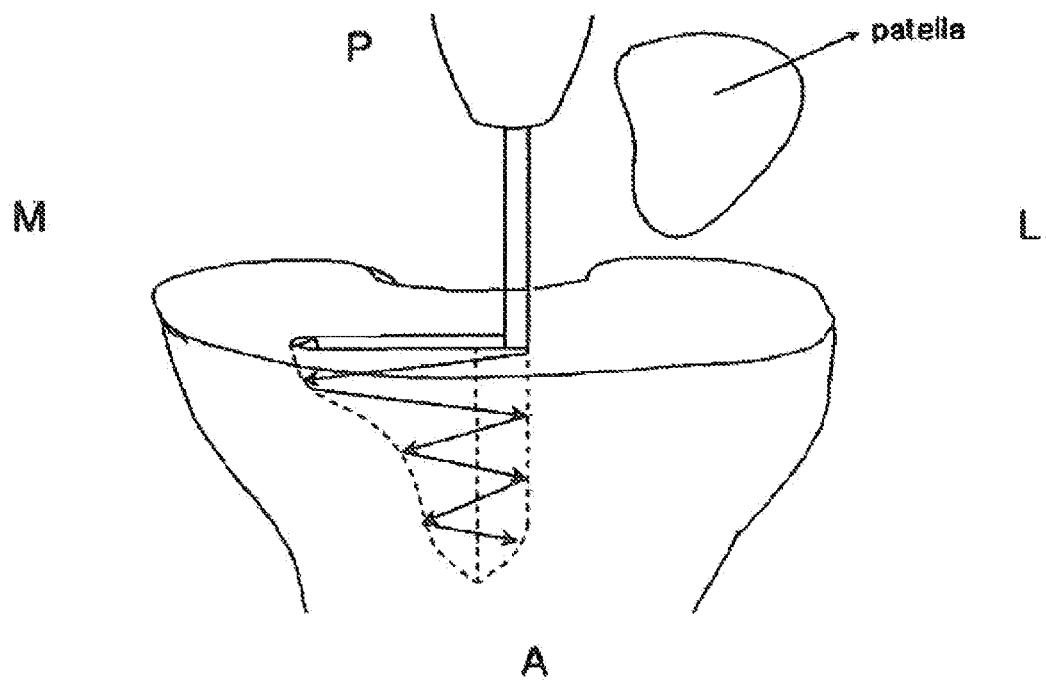

Referring to FIG. 25, a cruciform coupling groove for coupling an implant is cut in the surface of the lower bone of the knee joint. From this time, the cutter having the small-sized cantilever (having the length of 20~30 mm and the diameter of 1.5~4.0 mm) is used.

The coupling groove is defined by cutting a medial portion through a countersinking technique. The groove defined to have a prescribed depth has the shape in which the top is wide and the bottom is narrow, that is, the shape of an inverted triangle. Through this, the fixing part of the implant can be easily coupled into the groove.

When cutting the groove, since the patella is positioned at all time at a distance of several millimeters from the lower bone of the knee joint, as the surgeon slightly retracts the patella outward, it is possible to prevent the soft tissues from being damaged by the cutter.

Figure 26:
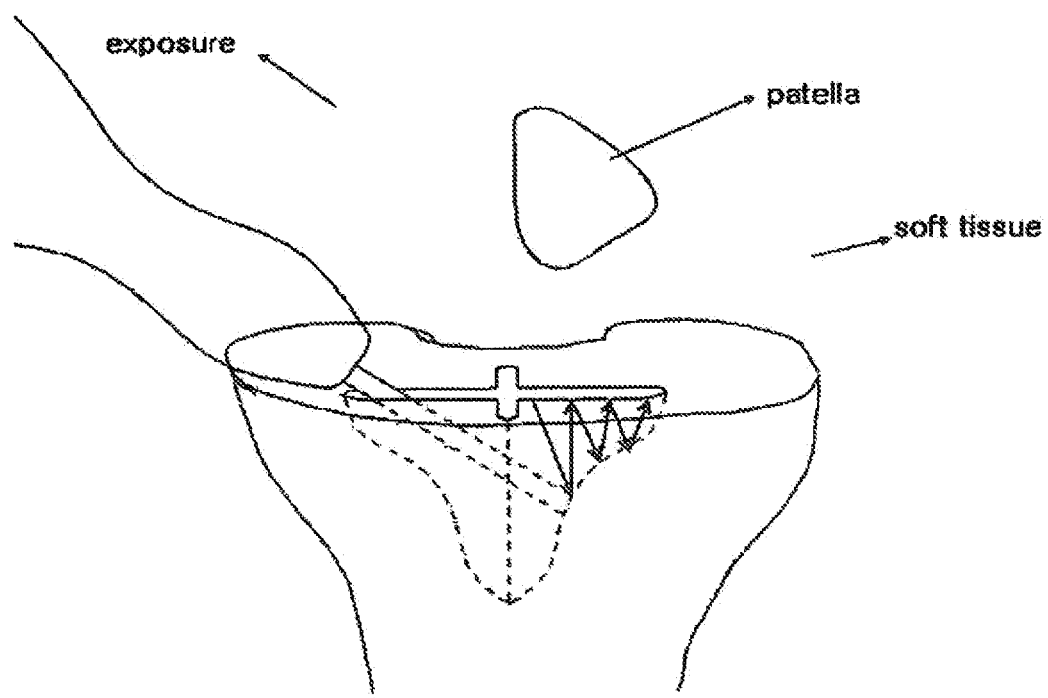
Figure 27:
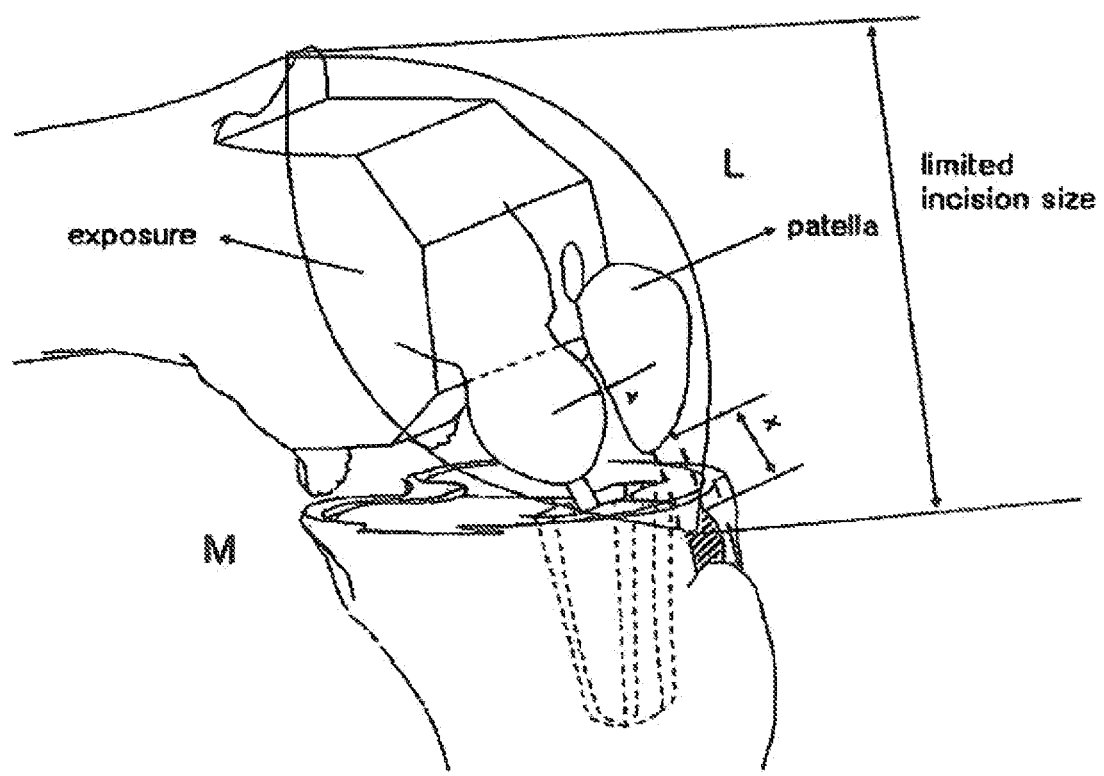

Referring to FIGS. 26 and 27, in order to define the cruciform groove in the lateral portion, the cutter is used in the medially slanted state as shown by the arrows in the drawing to define a tunnel in the bone.

By the countersinking technique devised to define a groove in this way, the cutting of the groove of the cruciform along the M-L line can be optimized.

In this regard, since the patella is freely positioned and the surrounding soft tissue and the patella are positioned at all time at a distance of several millimeters from the lower bone of the knee joint, as the surgeon slightly retracts the patella outward, it is possible to prevent the soft tissues from being damaged by the cutter.

This maneuver is to avoid any injury by way of stretching, tearing and impinging of the patella ligament which can be caused due to the minimal invasive surgery.

Figure 28:
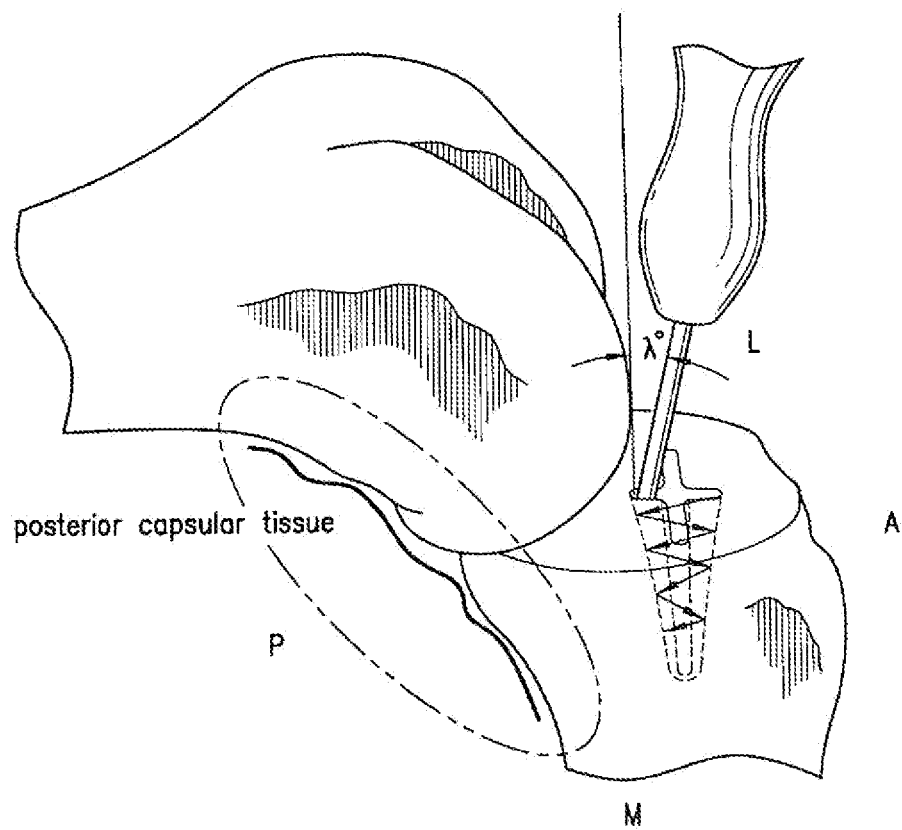

Referring to FIG. 28, the cutting of the anterior-posterior groove of the cruciform is performed by slanting anteriorly the cutter by a prescribed angle of $\lambda°$ with respect to the axis of the implant and the lower bone of the knee joint.

This maneuver is to prevent the sleeve and the cutter from impinging upon the upper bone of the knee joint.

In the conventional method, in order to prevent the impingement upon the bone, the cutter coupled to the arm of a robot is moved parallel to the axis of the implant, and the lower bone of the knee joint is moved anterior with respect to the posterior condyle of the femur so as to prevent the impingement between the cutter and the sleeve and the upper bone of the knee joint.

The posterior movement of the lower bone of the knee joint is likely to cause the stretching and tearing of the posterior capsule. In the present invention, by slanting the cutter by the prescribed angle of $\lambda°$, the posterior movement or widening becomes unnecessary.

Figure 29:
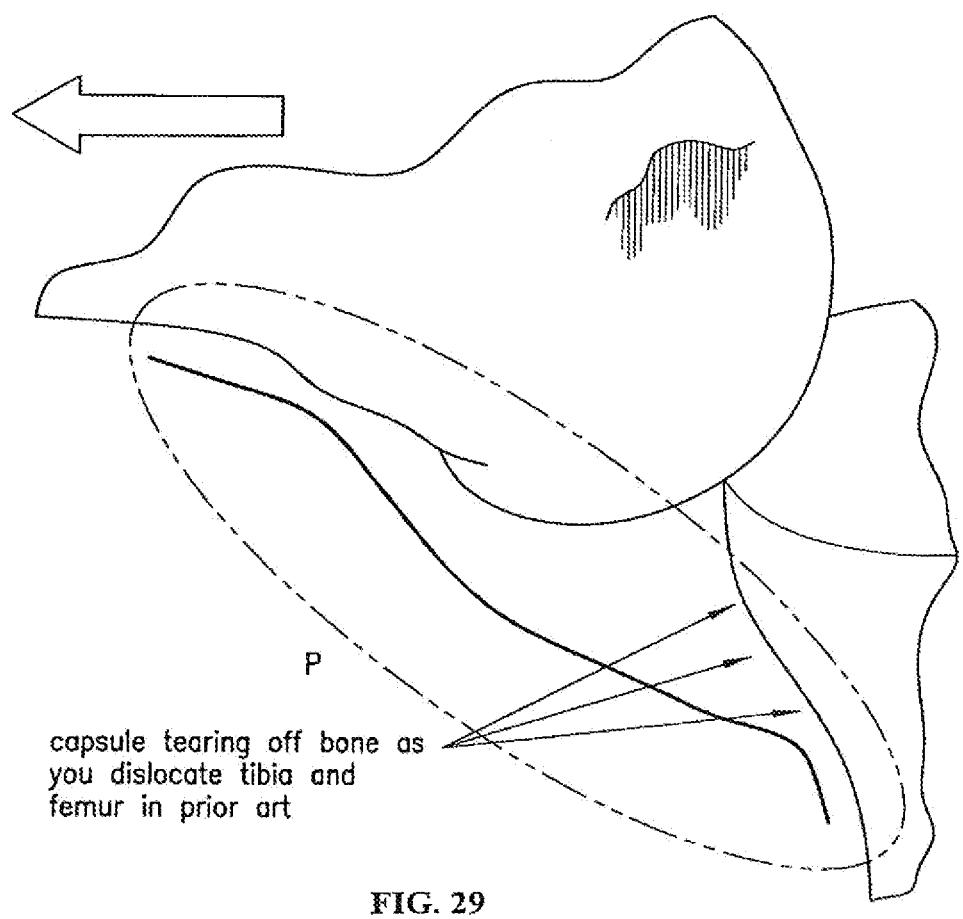

Referring to FIG. 29, after the seating surfaces for the implant are defined through the cutting of the upper bone and the lower bone of the knee joint as described above, by attaching the implant to the respective seating surfaces, the knee joint arthroplasty can be primarily finished.

In the cutting system for implementing the surgery through the tunnel cutting method as described above, the cutter, i.e., the cantilever of the present invention is minimized in its diameter to minimize the thickness of a cut portion so that the bone to be secondarily removed later can have a substantial thickness and therefore can serve as a safety shield for protecting surrounding tissue. It is required that the cutter is manufactured to have a maximum length as long as the breakage of the cutter is prevented.

As a result, the present invention suggests the optimum cutting system in the method for cutting the knee joint using a robot through the tunnel cutting technique.

Figure 30:
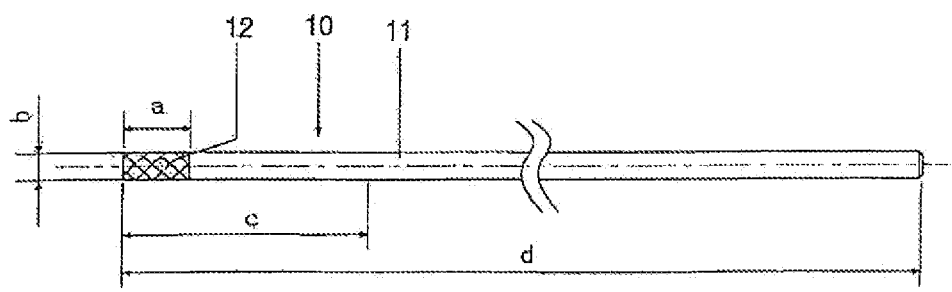
FIG. 30 is a side view illustrating a system for cutting the knee joint using a robot in accordance with another embodiment of the present invention.

FIG. 30 is a side view illustrating a system for cutting the knee joint using a robot in accordance with another embodiment of the present invention.

In the system for cutting the knee joint according to the present invention, a cutter 10 has the shape of a round bar which has a constant diameter.

Also, the cutter 10 has a shaft 11 in which most axial portion thereof is rotatably supported in the sleeve 14 and is coupled at the rear (proximal) end thereof to the motor M to be integrally rotated therewith and the remaining axial portion thereof has the shape of a cantilever extending out of the sleeve 14, and a head 12 which is formed on the distal end of the shaft 11 which extends out of the sleeve 14.

At this time, the shaft 11 of the cutter 10 must have a minimum diameter 'b', and the length 'c' of the cantilever extending out of the sleeve 14 is closely related with the diameter 'b' of the shaft 11. The shaft 11 must have a length 'd' greater than the length 'c' of the cantilever to be appropriately supported by the sleeve 14 and the motor M.

If the procedure for cutting the bone using the cutter manufactured to satisfy the conditions given in the present invention is not provided, the longer cantilever will require the larger cutter shaft diameter. Therefore, the bone left after cutting to be secondarily removed later (which serves as the safety shield) cannot but be decreased in the thickness thereof due to the large cutter shaft diameter, and therefore, cannot properly serve as the safety shield and is likely to be unintentionally removed from the knee joint.

Figure 31:
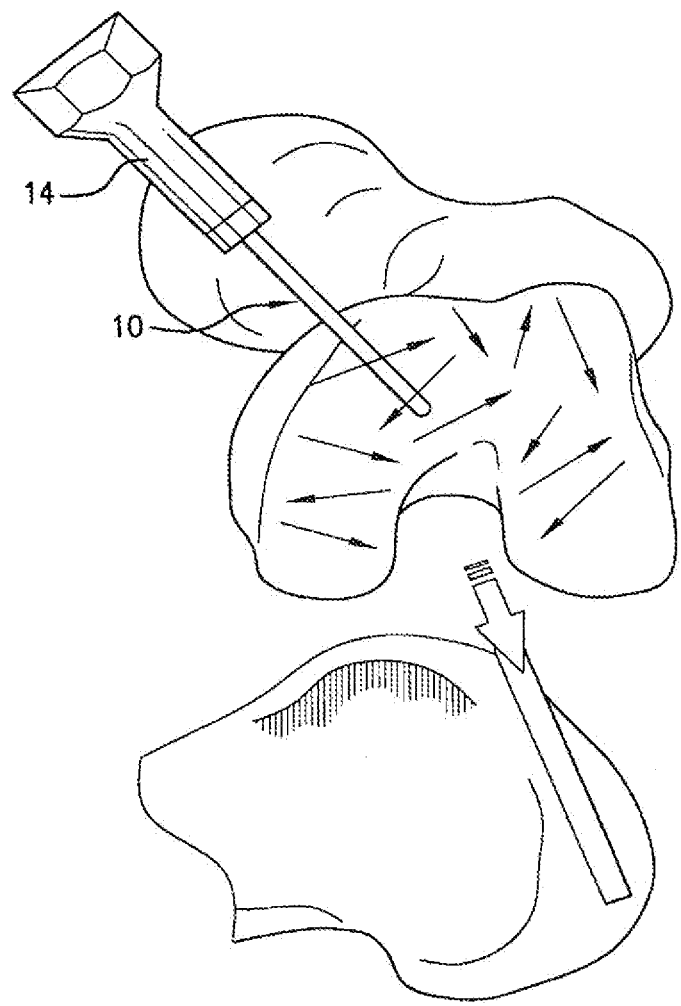
FIG. 31 is a schematic view illustrating the use of the system for cutting the knee joint using a robot in accordance with another embodiment of the present invention.

FIG. 31 is a schematic view illustrating the use of the system for cutting the knee joint using a robot in accordance with another embodiment of the present invention, and shows the tunnel cutting method implemented along the arrows.

Meanwhile, in the present invention, when the cantilever length 'c' of the cutter 10 is 20~30 mm and the diameter 'b' of the shaft 11 is less than 2.5 mm, the aforementioned partial or divided cutting of the bone can be performed in a satisfactory manner.

That is to say, in the partial cutting, as described above, by maximizing the length 'c' of the cantilever in proportional to the diameter and minimizing the diameter 'b' of the shaft 11, the thickness of the remnant bone can be maximized so that the remnant bone can serve properly as the safety shield for preventing the surrounding tissue from being damaged.

Figure 32:
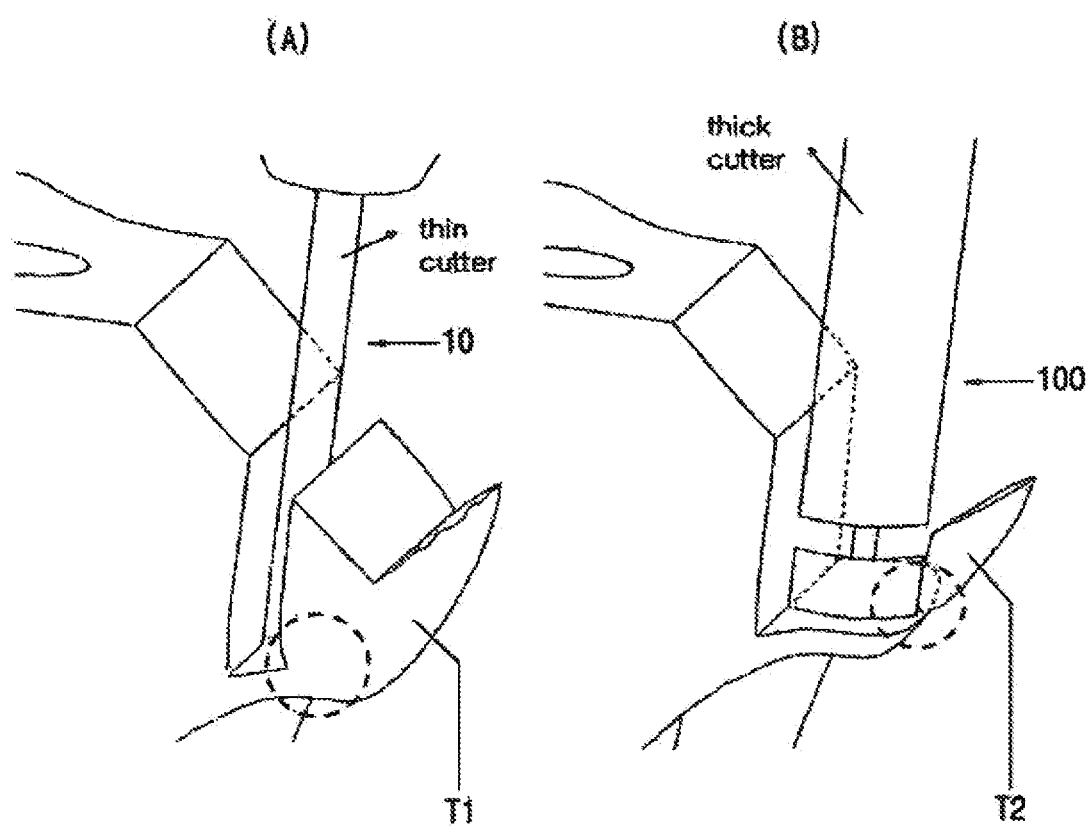
FIG. 32 is schematic views comparing the thicknesses of remnant bone depending upon the shapes of cutters in the use of the system for cutting the knee joint using a robot in accordance with another embodiment of the present invention.

This principle can be readily understood from the fact that, as shown in FIG. 32, the slender cutter 10 (see A) of the present invention can leave thick remnant bone T1 and the thick cutter (see B) of the conventional art can leave thin remnant bone T2.

Figure 33:
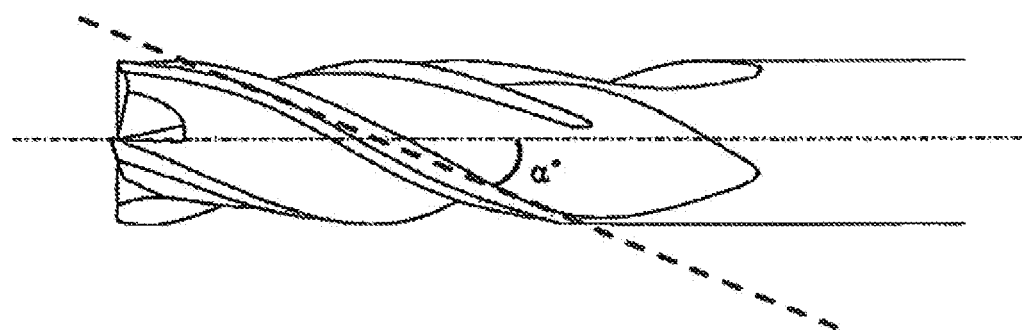
FIG. 33 is an enlarged view illustrating the side cutting feature of the cutter in the system for cutting the knee joint using a robot in accordance with another embodiment of the present invention.
Figure 34:
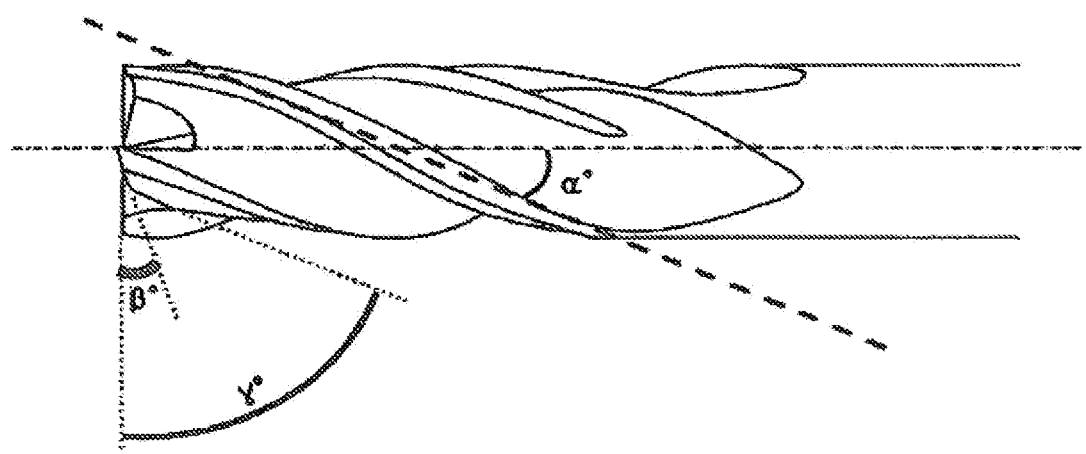
FIG. 34 is an enlarged view illustrating the end cutting feature of the cutter in the system for cutting the knee joint using a robot in accordance with another embodiment of the present invention.

FIGS. 33 and 34 are enlarged views illustrating the side cutting part and the end cutting part of the cutter head 12, wherein a helix angle of α° is formed in the cutting edges of the side cutting part.

The helix angle of α° is to facilitate the discharge of chips when performing cutting. If the helix angle is too large, the cutter is made aggressive and therefore the bone is likely to be overcut. Also, if the helix angle is too small, great cutting force is required so that the cutter is likely to be deformed and undercut of the bone can be caused.

Accordingly, in the present invention, the helix angle is set to 10~20° so that the cutting of the uneven density bone can be optimally performed.

Figure 35:
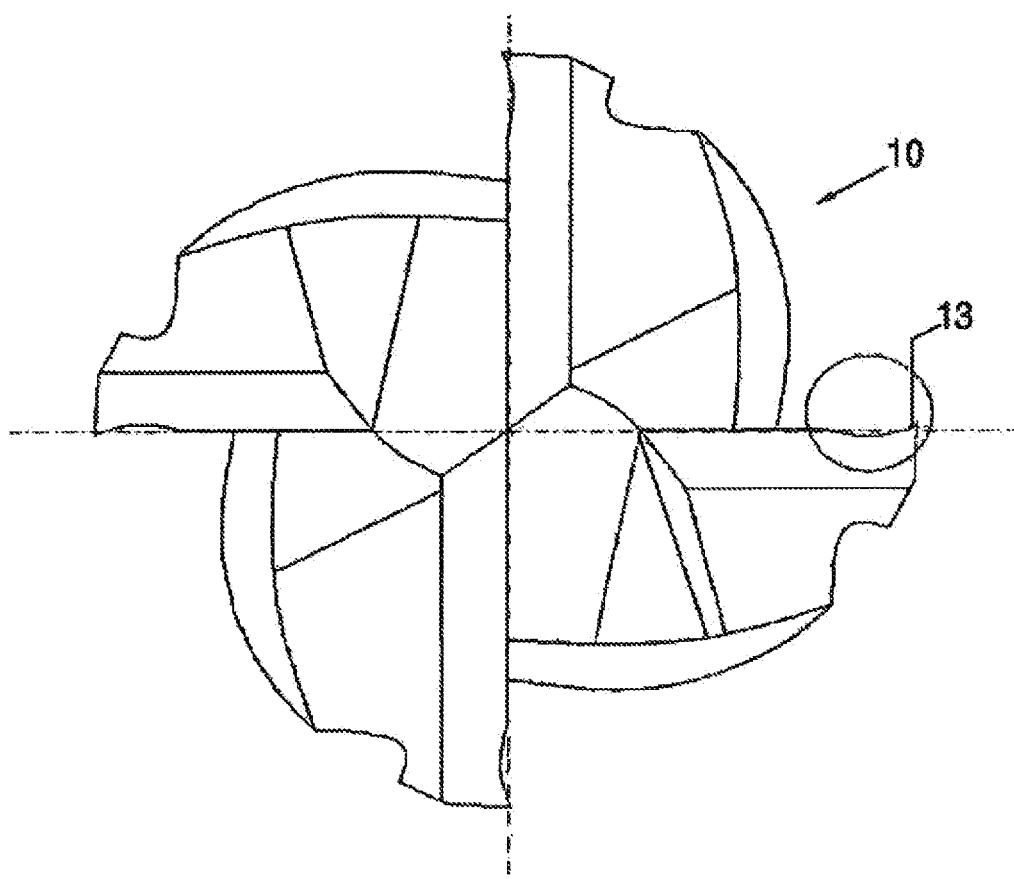
FIG. 35 is a bottom view illustrating the head of the cutter in the system for cutting the knee joint using a robot in accordance with another embodiment of the present invention.
Figure 36:
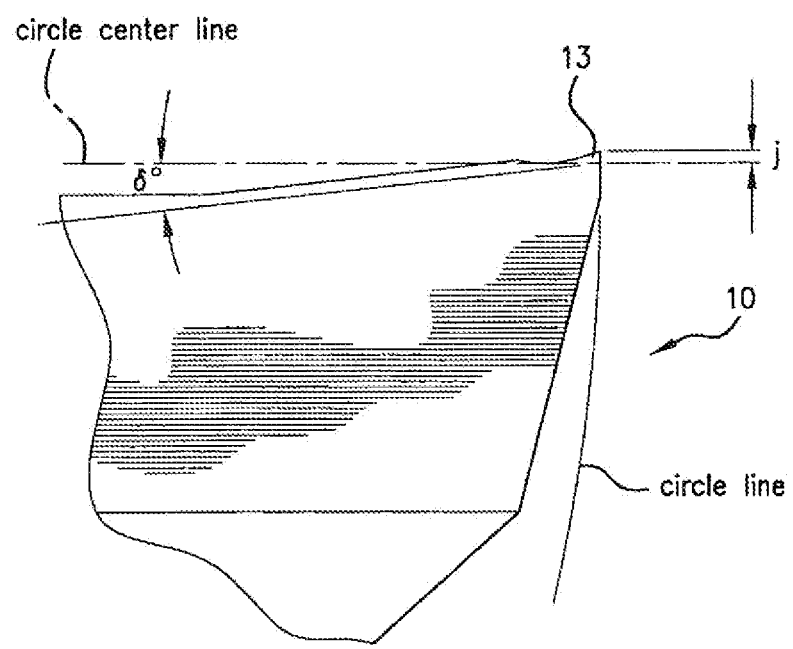
FIG. 36 is an enlarged view illustrating the chatter blocker of the cutter in the system for cutting the knee joint using a robot in accordance with another embodiment of the present invention.

FIG. 35 illustrates the distal end of the cutter head 12, and FIG. 36 is an enlarged view of the chatter blockers of the cutter head 12.

The safety factor in the design of the cutter head 12 is the provision of chatter blockers 13.

In the present invention, the chatter blockers 13 are formed to be offset by an amount of 'j' with respect to the diametric center line.

The chatter blockers 13 are positioned on the circle line and on the diametric center line of the cutter and have the shape of an aggressive rake or a hook to render the effect of pulling the bone so that vibrations and chattering can be reduced during cutting.

At this time, this chatter prevention technique plays an important role of preventing the bone from being overcut.

Also, in order to further stabilize the cutting system, it is preferred that the cutter shaft 11 be designed to be further slender so as to increase the stiffness. The slender cutter shaft 11 can double the tunnel cutting profiles and characteristics.

Figure 37:
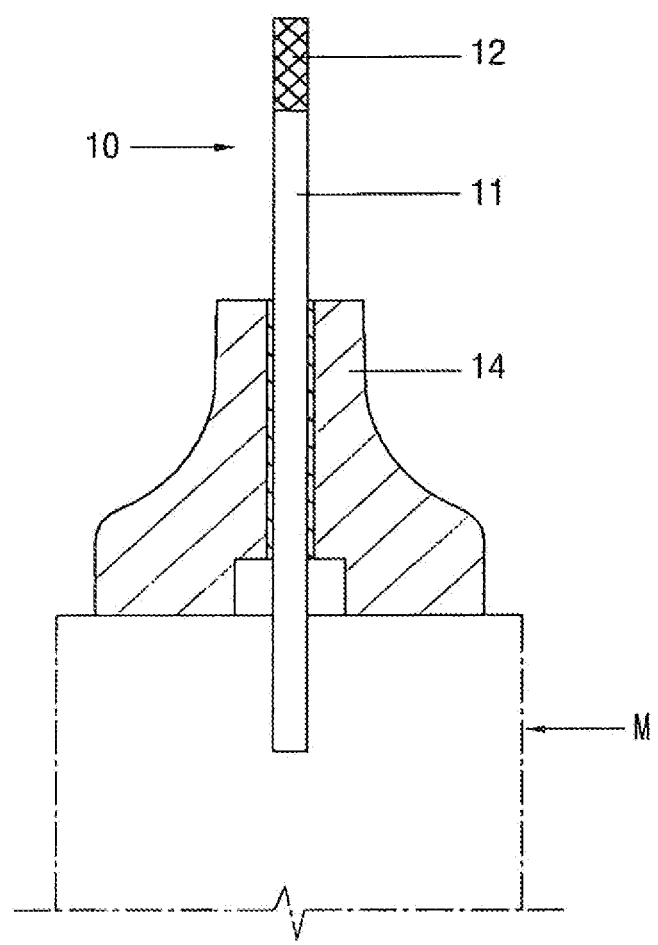
FIG. 37 is a side sectional view illustrating the state in which a short cantilever cutter and a sleeve are assembled with each other in the system for cutting the knee joint using a robot in accordance with another embodiment of the present invention.
Figure 38:
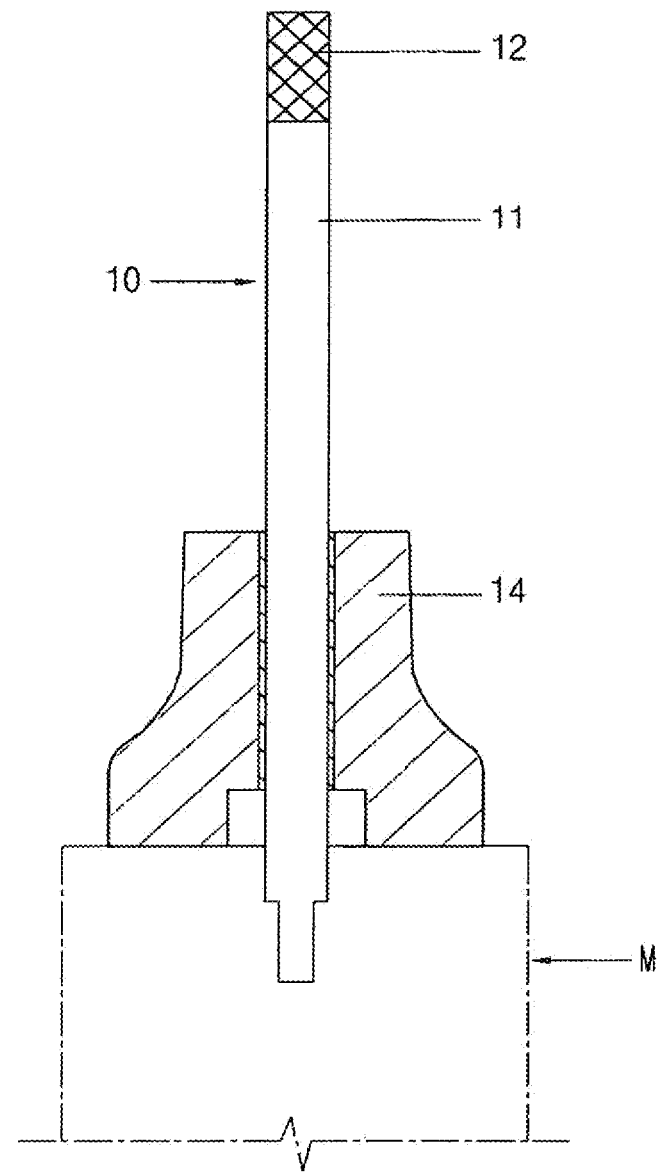
FIG. 38 is a side sectional view illustrating the state in which a long cantilever cutter and a sleeve are assembled with each other in the system for cutting the knee joint using a robot in accordance with another embodiment of the present invention.
Figure 39:
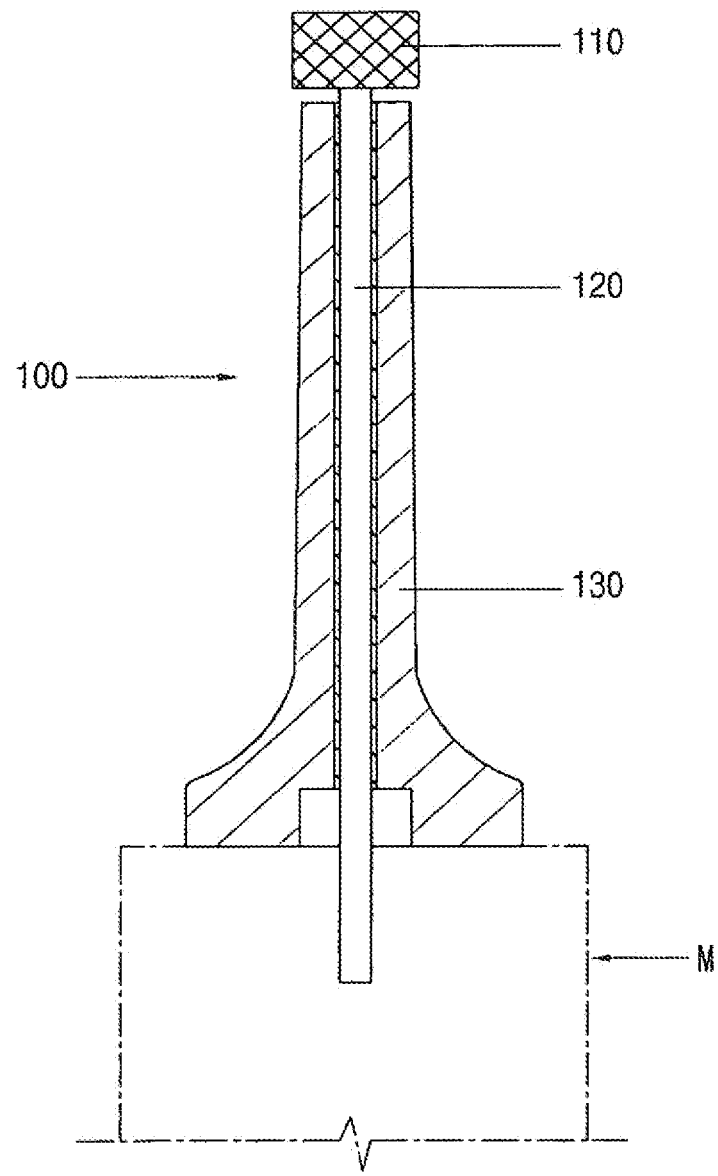
FIG. 39 is a side sectional view illustrating the cutter used in a conventional top down milling method for total knee replacement arthroplasty.
Figure 40:
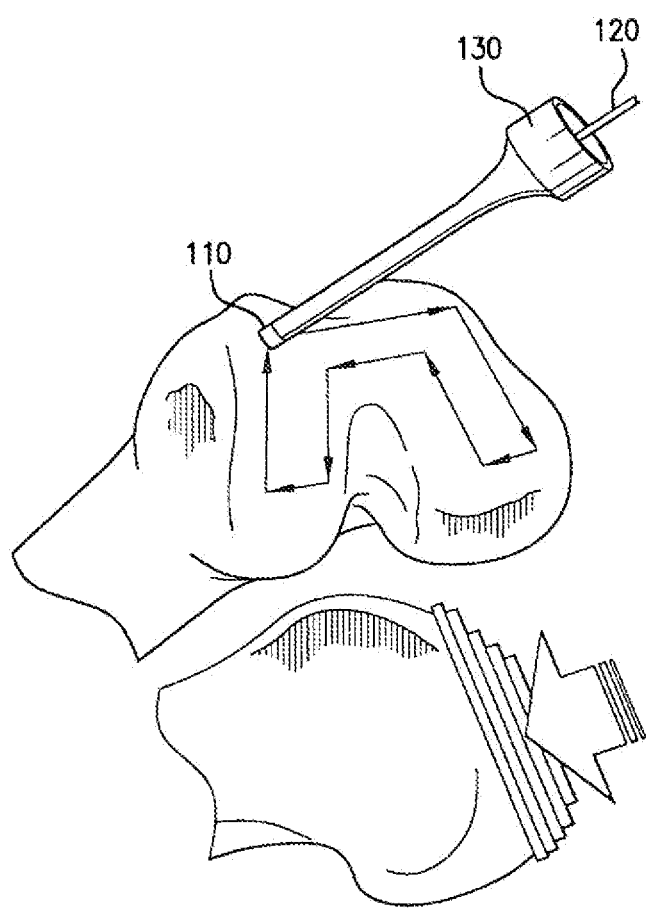
FIG. 40 is a schematic view illustrating the conventional top down milling method for total knee replacement arthroplasty.

FIGS. 37 and 38 illustrate the shapes of cantilevers depending upon the configurations of cutters, with cutters 10 coupled to sleeves 14.

FIG. 37 illustrates a short cantilever type design in which the diameter of the cutter shaft and a sleeve assembly cooperatively reinforce stiffness.

In other words, in order to minimize the thickness of the cut portion of the bone and thereby increase the thickness of the remnant bone, the cutter has a minimum diameter and a maximum length, that is, a most appropriate cantilever length, in proportion to the diameter, so that the cutter can be suitably used for partial cutting of the knee joint while being prevented form being broken due to cutting resistance. This cutter performs almost all of the cutting operation in the present invention.

FIG. 38 illustrates a long cantilever type design in which the diameter of the cutter shaft provides stiffness to the system and a short sleeve including a bearing rotatably holds the cutter 10.

At this time, the long cantilever is used when cutting the planar portion of the lower bone of the knee joint. Since the planar portion has a large area and the cutter can be relatively freely introduced onto the planar portion, in order to rapidly perform the cutting operation, the cutter having the larger diameter and the longer length than the cutter used for cutting the upper bone of the knee joint is used.

The head and the shaft of the cutter have the same diameter.

The cantilevered cutter according to the present invention, configured as described above, is fitted into the sleeve to be rotatably supported therein, and is used in a state in which it is mounted to the arm of a preselected cutting system, that is, a surgical robot having multi-degree of freedom.

For example, the cutter 10 is positioned on the distal end of the position-changeable arm of a robot and performs the cutting operation by receiving power.

As is apparent from the above description, the method and the system for cutting the knee joint using a robot according to the present invention confer advantages as described below.

First, since surgery is performed for portions of the knee joint to be cut, in a tunnel cutting technique using a cantilevered cutter which is optimized to have a minimum diameter and a maximum length, the bone can be quickly and safely cut, and the damage to the muscle or surrounding soft tissue attached to the bone can be minimized.

Second, in place of the conventional method in which a cutter is moved in sideward directions only from the anterior side of the knee joint and cut the bone through milling, a tunnel cutting method is adopted in which the bone is cut by introducing the distal end of the cutter medially or laterally not only from the anterior side of the knee joint but also from the posterior side of the knee joint without causing impingement between the cutter and surrounding tissue such that the path of the cutter is optimized. As a consequence, the surgery can be performed with minimum incision of the skin without requiring excessive retraction of the surrounding soft tissue such as the skin, the flesh, the muscle and the ligament.

Accordingly, because the soft inside of the bone (the soft bone) as well as the hard outside of the bone (the hard bone) of an arthritis patient can be precisely and finely cut, a margin can be provided to a surgeon while performing surgery, and enough satisfaction can be provided to the patient due to rapid recovery after the surgery.

When considering the fact that future surgical operation will require quickness and precision more than other industrial fields, it is obvious that the surgery-related products using robots will occupy a substantial portion of the medical equipment market. Therefore, the present invention provides industrially applicable up-to-date technology in relation with robotic surgery so as to accommodate the trend of the medical equipment market.

Although preferred embodiments of the present invention have been described for illustrative purposes, those skilled in the art will appreciate that various modifications, additions and substitutions are possible, without departing from the scope and the spirit of the invention as disclosed in the accompanying claims.

What is claimed is:

1. A method for safely cutting a bone, comprising:
    identifying a starting point on an upper bone of a knee joint exposed by minimal retraction of surrounding tissue, the starting point located below a piece of remnant bone to be formed as a safety shield to the surrounding tissue;
    introducing via a robot, a rotary cutter comprising a shaft, a portion of the shaft supported within a sleeve and a remaining portion of the shaft serving as a cantilever extending out of the sleeve and having a cutting head at a distal end of the remaining portion of the shaft, into the upper bone at the starting point until a prescribed distance between the upper bone and the sleeve is obtained;
    pivoting the head of the cutter medially within the upper bone from the starting point to each edge of the upper bone and forming the remnant bone piece, wherein the remnant bone piece is separated from the upper bone along a remaining connected portion along the remnant bone piece and the upper bone;
    cutting a circle into a distal surface of the upper bone forming an island within the circle; and
    removing the island from the circle.

2. The method according to claim 1, wherein a plane surface is formed on the upper bone upon removal of the remnant bone piece.

3. The method according to claim 2, further comprising at least one of:
    forming one or more further plane surfaces on the upper bone at an angle from the plane surface; and
    forming an even further plane surface on the upper bone at a further angle from one of the further plane surfaces.

4. The method according to claim 1, further comprising:
    cutting the upper bone of the knee joint by moving the cutter parallel to a Whiteside's line.

5. The method according to claim 1, further comprising:
    cutting the upper bone of the knee joint by moving the cutter to a prescribed angle with respect to a Whiteside's line avoiding impingement between the cutter and at least one of a patella and a ligament structure.

6. The method according to claim 1, further comprising:
    overcutting the upper bone forming the remnant bone piece, and
    removing the remnant bone piece using on the overcut.

7. The method according to claim 1, further comprising:
    making three separate cuts in different directions on a proximal surface of a lower bone of the knee joint to form a single plane.

8. The method according to claim 7, wherein the different directions comprise a direction at an angle to a medial-lateral line, a direction parallel to the medial-lateral line and a direction parallel to an anterior-posterior line.

9. The method according to claim 7, wherein the plane is formed by moving the cutter in a zigzag pattern during each of the three separate cuts.

10. The method according to claim 7, wherein the cuts of the lower bone of the knee joint form a safety rim along an edge of the plane to prevent damage to surrounding soft tissue.

11. The method according to claim 7, further comprising:
    forming a cruciform groove within the lower bone of the knee joint by cutting in medial, lateral, anterior and posterior directions.

12. The method according to claim 11, wherein, the cutting in the lateral direction of the lower bone of the knee joint is conducted with the cutter slanted.

* * * * *